(12) United States Patent  
Orosa et al.

(10) Patent No.: US 8,715,771 B2  
(45) Date of Patent: May 6, 2014

(54) COATED STENT AND METHOD OF MAKING THE SAME

(75) Inventors: Dennis R. Orosa, San Diego, CA (US); John E. Papp, Temecula, CA (US); Hung T. Nguyen, San Diego, CA (US); Stephen D. Pacetti, San Jose, CA (US); Dudley Shelton Jayasinghe, Murrieta, CA (US); Matthew J. Gillick, Murietta, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 751 days.

(21) Appl. No.: 12/563,045

(22) Filed: Sep. 18, 2009

(65) Prior Publication Data

US 2010/0104734 A1    Apr. 29, 2010

Related U.S. Application Data

(60) Continuation-in-part of application No. 12/112,935, filed on Apr. 30, 2008, and a continuation-in-part of application No. 11/825,443, filed on Jul. 5, 2007, which is a division of application No. 10/375,497, filed on Feb. 26, 2003, now Pat. No. 7,255,891.

(60) Provisional application No. 60/915,355, filed on May 1, 2007, provisional application No. 61/186,726, filed on Jun. 12, 2009, provisional application No. 61/186,742, filed on Jun. 12, 2009, provisional application No. 61/277,114, filed on Sep. 18, 2009.

(51) Int. Cl.  
*B05D 3/00* (2006.01)

(52) U.S. Cl.  
USPC .................. 427/2.24; 427/2.2; 427/2.25

(58) Field of Classification Search  
USPC ........................................... 427/2.3  
See application file for complete search history.

(56) References Cited

U.S. PATENT DOCUMENTS

| | | | |
|---|---|---|---|
| 4,977,901 | A | 12/1990 | Ofstead |
| 5,112,457 | A | 5/1992 | Marchant |
| 5,328,471 | A | 7/1994 | Slepian |
| 5,455,040 | A | 10/1995 | Marchant |
| 5,464,650 | A | 11/1995 | Berg et al. |
| 5,505,984 | A | 4/1996 | England et al. |
| 5,578,073 | A | 11/1996 | Haimovich et al. |
| 5,599,576 | A | 2/1997 | Opolski |
| 5,605,696 | A | 2/1997 | Eury et al. |

(Continued)

FOREIGN PATENT DOCUMENTS

| | | |
|---|---|---|
| EP | 0 665 023 | 8/1995 |
| EP | 0 970 711 | 1/2000 |

(Continued)

*Primary Examiner* — Dah-Wei Yuan  
*Assistant Examiner* — Andrew Bowman  
(74) *Attorney, Agent, or Firm* — Squire Sanders (US) LLP

(57) ABSTRACT

A coated implantable medical device and a method of coating an implantable medical device is disclosed, the method includes applying a composition onto the device and drying the composition at elevated temperature in an environment having increased relative humidity. A pre-screening method for a manufacturing lot of coated stents to determine the number of drug coating layers for a desired drug release rate is disclosed. The method including coating and testing small groups of stents, and applying the results of the tests to determine the number of drug coating layers to apply to the manufacturing lot of stents.

10 Claims, 9 Drawing Sheets

(56) References Cited

U.S. PATENT DOCUMENTS

| | | |
|---|---|---|
| 5,667,767 A | 9/1997 | Greff et al. |
| 5,670,558 A | 9/1997 | Onishi et al. |
| 5,679,400 A | 10/1997 | Tuch |
| 5,700,286 A | 12/1997 | Tartaglia et al. |
| 5,716,981 A | 2/1998 | Hunter et al. |
| 5,762,944 A | 6/1998 | Inoue et al. |
| 5,824,049 A | 10/1998 | Ragheb et al. |
| 5,830,178 A | 11/1998 | Jones et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,873,904 A | 2/1999 | Ragheb et al. |
| 5,879,878 A | 3/1999 | Raguse et al. |
| 5,971,954 A | 10/1999 | Conway et al. |
| 5,980,928 A | 11/1999 | Terry |
| 5,980,972 A | 11/1999 | Ding |
| 6,015,541 A | 1/2000 | Greff et al. |
| 6,042,875 A | 3/2000 | Ding et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,584 A | 5/2000 | Krell et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,143,037 A | 11/2000 | Goldstein et al. |
| 6,153,252 A * | 11/2000 | Hossainy et al. ............ 427/2.3 |
| 6,165,212 A | 12/2000 | Dereume et al. |
| 6,235,340 B1 | 5/2001 | Lee et al. |
| 6,265,016 B1 | 7/2001 | Hostettler et al. |
| 6,270,831 B2 | 8/2001 | Kumar et al. |
| 6,428,616 B1 | 8/2002 | Neely, Jr. |
| 6,451,373 B1 | 9/2002 | Hossainy et al. |
| 6,596,402 B2 | 7/2003 | Soerens et al. |
| 6,607,598 B2 | 8/2003 | Schwarz et al. |
| 6,656,216 B1 | 12/2003 | Hossainy et al. |
| 6,716,444 B1 | 4/2004 | Castro et al. |
| 6,746,482 B2 | 6/2004 | Ung-Chhun |
| 6,844,028 B2 | 1/2005 | Mao et al. |
| 6,908,624 B2 | 6/2005 | Hossainy et al. |
| 6,939,376 B2 | 9/2005 | Shulze et al. |
| 2002/0065551 A1 | 5/2002 | Koole et al. |
| 2003/0054431 A1 | 3/2003 | Raguse et al. |
| 2004/0194704 A1 | 10/2004 | Chappa et al. |
| 2004/0208985 A1 | 10/2004 | Rowan et al. |
| 2004/0241325 A1 | 12/2004 | Al-lamee et al. |
| 2005/0125054 A1 | 6/2005 | Bhat et al. |
| 2006/0024426 A1 | 2/2006 | Akerman et al. |
| 2006/0128739 A1 | 6/2006 | Maryanoff et al. |

FOREIGN PATENT DOCUMENTS

| | | |
|---|---|---|
| WO | WO 00/12147 | 3/2000 |
| WO | WO 00/64506 | 11/2000 |
| WO | WO 01/01890 | 1/2001 |

\* cited by examiner

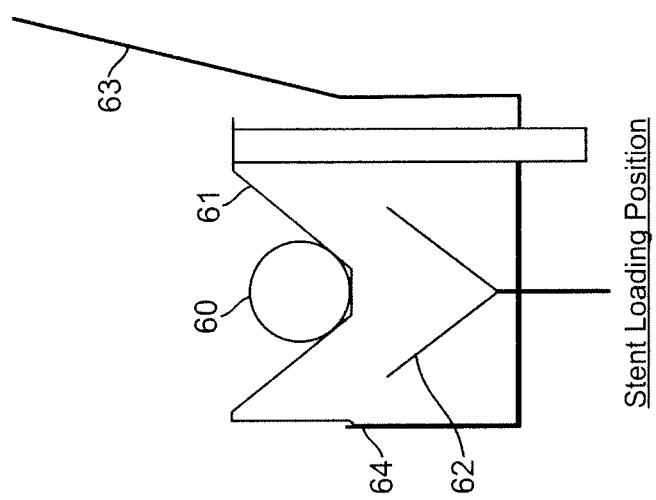
FIG. 5A  Stent Loading Position
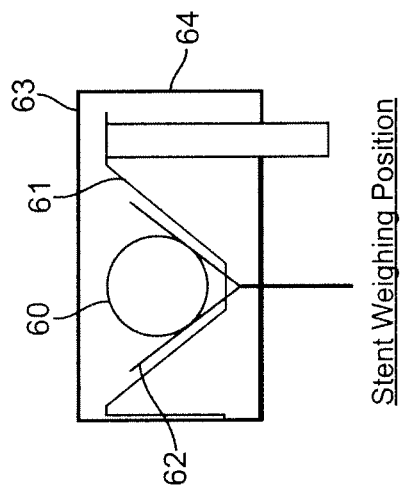
FIG. 5B  Stent Weighing Position

COATED STENT AND METHOD OF MAKING THE SAME

CROSS-REFERENCE

This application is a continuation-in-part of U.S. application Ser. No. 12/112,935, filed Apr. 30, 2008, which claims the benefit of U.S. Provisional Application No. 60/915,355, filed May 1, 2007; this application is also a continuation-in-part of U.S. application Ser. No. 11/825,443, filed Jul. 15, 2007, now U.S. Pat. No. 8,007,855, which is a divisional application of application Ser. No. 10/375,497, filed Feb. 26, 2003, now U.S. Pat. No. 7,255,891; this application also claims the benefit of U.S. Provisional Application No. 61/186,726, filed Jun. 12, 2009, and U.S. Provisional Application No. 61/186,742, filed Jun. 12, 2009, and U.S. Provisional Application No. 61/277,114, filed Sep. 18, 2009, the entire content of all of the above applications and patent incorporated by reference herein.

BACKGROUND OF THE INVENTION

1. Field of the Invention

This invention relates to methods for coating drug delivery devices.

2. Description of the Background

In the field of medical technology, there is frequently a necessity to administer drugs locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

The drug-eluting stent also provides for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. As such, local delivery thus produces fewer side effects and achieves more favorable results.

Peripheral artery disease affecting the lower extremities is common in an aging population, affecting 10-14% of men over the age of 65, and 20% of men and women reaching the age of 75. The progression of lower extremity arterial disease can lead to loss of mobility, limb pain, gangrene and amputation, as well as increased mortality. Mortality rates at five years in patients with Peripheral Vascular Disease (PVD) are approximately 30%; these rates reach 44% in patients with severe peripheral artery disease. The superficial femoral artery (SFA) is the most commonly diseased blood vessel in the peripheral (lower limb) vasculature, due to its characteristics: a long vessel surrounded by flexion points, with few collateral vessels. These characteristics promote more diffuse disease, and slow flow and flow dynamics.

Prevention of restenosis after endovascular treatment in the peripheral arteries is a major challenge for the interventionalist, particularly in the superficial femoral artery (SFA), in which long, heavily calcified, and/or chronically occluded lesions are often present. Self-expanding stents, with their elastic properties, have been shown to be of benefit in the revascularization of the SFA. Stent implantation, by providing a permanent scaffold for the vessel, reduces vessel recoil and remodeling, two of the contributing factors in restenosis. However, neointimal hyperplasia, the major mechanism of restenosis, remains a significant problem in the peripheral arteries.

Accordingly, to reduce the partial or total occlusion of the artery by the collapse of arterial lining, and to reduce the chance of the development of thrombosis and restenosis, an expandable, intraluminal prosthesis coated with a therapeutic or beneficial agent, one example of which includes a drug-eluting stent, is implanted in the lumen to maintain the vascular patency.

One method of medicating a stent is with the use of a polymer coating incorporating a drug. To fabricate the polymer coating, a suitable polymer is usually dissolved in a solvent or blend of solvents, followed by applying the solution onto the stent, for example, by spraying or dipping. To complete the process of fabricating the stent coating, the stent is dried and/or baked to remove the solvent.

Examples of solvents currently used to dissolve biocompatible polymers for fabricating stent coatings include dimethylacetamide (DMAC), dimethylsulfoxide (DMSO), dimethylformamide (DMF), and formamide. These solvents or similar solvents with relatively high boiling points, for example, above 120° C. at ambient pressure, and/or low volatility, for example, having vapor pressure under 15 Ton at room temperature, have a tendency to evaporate very slowly. Prolonged period of time may be needed to allow the solvent to fully evaporate from the coating because residual or trace amounts of the solvent may remain in the coating composition, which may produce an adverse response subsequent to the stent implantation. Baking of the stent at relatively high temperatures may be needed to facilitate the process of the solvent removal. The baking temperatures used for this purpose, should not exceed the temperature at which the drug can be adversely affected, however. The embodiments of the present invention provide methods for facilitating the evaporation of the solvent from the coating composition.

Therefore, a need exists for a drug eluting implantable medical device, with a low residual solvent content, that via local application of therapeutic agents provides for an effective pharmacokinetic (PK) profile of drug tissue concentration over time and successfully inhibits or reduces restenosis in peripheral arteries.

SUMMARY

A method for coating an implantable medical device is provided, the method comprises applying a polymer composition onto the device, the polymer composition including a solution of a polymer in a solvent, and drying the polymer composition for a period of time at a drying temperature higher than the room temperature in a humid environment. The drug is present at an amount of at least 150 μg/cm$^2$ of stent surface area and the final stent coating has been dried in a humid environment. The resulting residual solvent level in μg is less than [(stent length (mm))×(2.634)]−(36.08). Useful polymers are vinyl polymers, urethane-based polymers, polyesters, and polysaccharides.

A method of coating a manufacturing lot of medical devices is disclosed, the method comprising the utilization of pre-screen devices subjected to coating and loading procedures to allow adjustment in the coating process such that the manufacturing lot will have the desired properties when subjected to the same processes.

BRIEF DESCRIPTION OF THE DRAWINGS

The disclosed subject matter will now be described in conjunction with the accompanying drawings in which:

FIGS. 5A and 5B are illustrations of a microbalance useful in accordance with the present invention;

DETAILED DESCRIPTION

A coating for an implantable medical device, such as a stent, can include an optional primer layer, a drug-polymer layer, and an optional topcoat layer. The drug-polymer layer can be applied directly onto the stent surface to serve as a reservoir for an active agent or a drug which is incorporated into the drug-polymer layer. An optional primer layer can be applied between the stent and the drug-polymer layer to improve the adhesion of the drug-polymer layer to the stent. An optional topcoat layer can be used to reduce the rate of release of the drug from the reservoir.

Medical Device Structure

The devices and methods presented can be used for treating the lumen of a patient. Generally, the present invention includes drug eluting implantable medical devices such as endoprostheses, vena cava filters, embolic protection filters, and the like that are configured with controlled drug delivery profiles that allow for enhanced drug delivery into the lumen tissue adjacent to the implantable medical device and that inhibits drug delivery into the systemic blood circulation. In accordance with a preferred embodiment, the implantable medical device is a stent. Preferably, the present invention includes a drug-eluting stent that has a stent body, a polymeric coating, and a therapeutic agent. Preferably, the therapeutic agent is a cytostatic agent. The polymeric coating is provided on the stent to facilitate the loading or delivery of the therapeutic agent. In accordance with a preferred embodiment, the polymeric coating is a poly(ethylene-co-vinyl alcohol).

Figure 1:
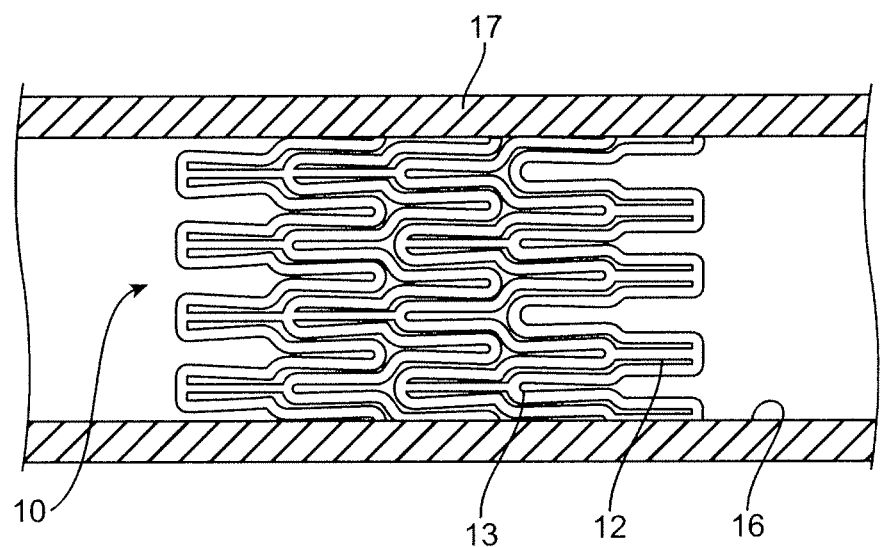
FIG. 1 is an planar view, partially in section, showing the expanded stent within the vessel in accordance with one embodiment of the invention.
Figure 2:
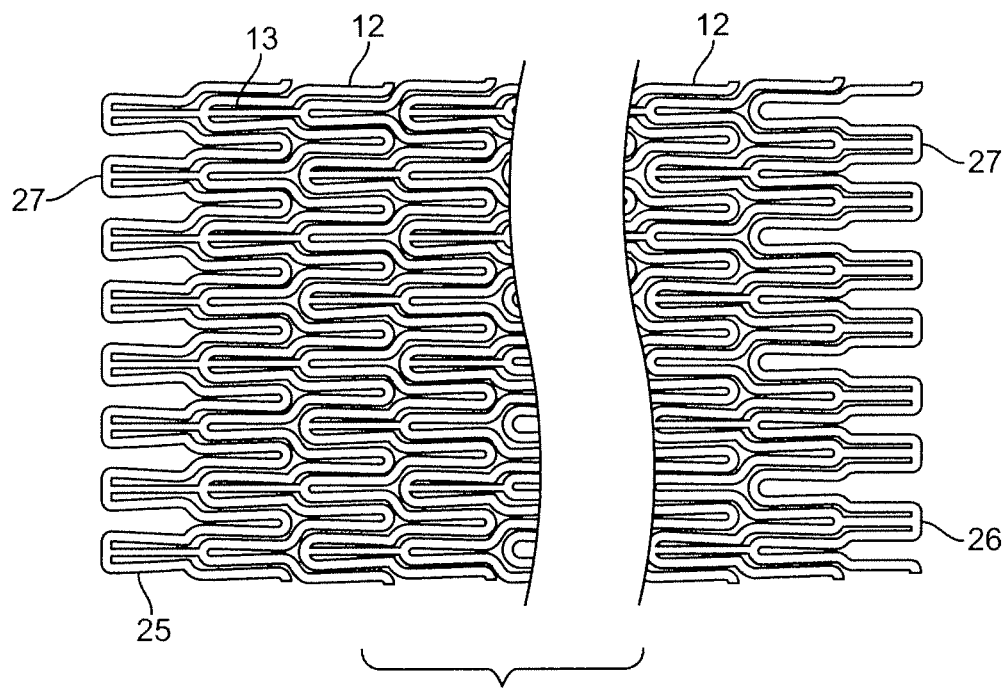
FIG. 2 is a planar view of a flattened stent in accordance with an embodiment of the of the present invention, which illustrates the serpentine pattern including peaks and valleys which form the cylindrical elements of the stent.
Figure 3:
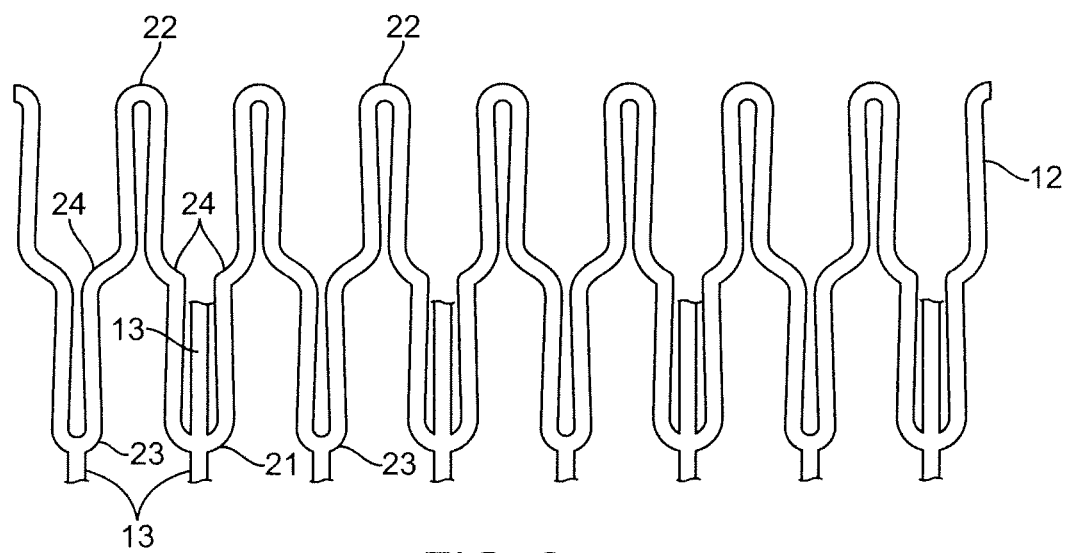
FIG. 3 is an enlarged partial view of the stent of FIG. 2 depicting the serpentine pattern along with the peaks and valleys which form an embodiment of a cylindrical element made in accordance with the present invention.

The structural body of the stent can be coated with at least one polymeric coating, such as poly(ethylene-co-vinyl alcohol) (i.e., EVAL), that functions as a drug delivery system that controls the release of drug contained therein. The drug contained within the polymer coating can be a cytostatic drug or other drug useful for inhibiting cell proliferation within the vascular lumen. The drug can be any drug having a therapeutic benefit for treating and/or preventing a disease or condition. The polymer coating that contains the drug can also be coated by another layer of the same or different polymer that further controls the release of the drug For purpose of illustration and not limitation, FIGS. 1-3 illustrate an exemplary stent that can be used in accordance with the present invention. As illustrated in FIG. 1, the stent 10 serves to hold open the artery 16 after delivery catheter is withdrawn. Due to the formation of stent 10, the undulating component of the cylindrical elements of stent 10 is relatively flat in a transverse cross-section so that when stent 10 is expanded, cylindrical elements 12 are pressed into the wall of artery 16 and as a result do not interfere with the blood flow through artery 16. Cylindrical elements 12 of stent 10 that are pressed into the wall of artery 16 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 16.

The stresses involved during expansion from a low profile to an expanded profile are generally evenly distributed among the various peaks and valleys of stent 10. Referring now to FIGS. 2 and 3, each expanded cylindrical element 12 embodies a serpentine pattern having a plurality of peaks and valleys that aid in the even distribution of expansion forces. In this exemplary embodiment, interconnecting members 13 serve to connect adjacent valleys of each adjacent cylindrical element 12 as described above. The various peaks and valleys generally have U, W and inverted-U shapes, in a repeating pattern to form each cylindrical element 12. It should be appreciated that the cylindrical element 12 can be formed in different shapes without departing from the spirit and scope of the present invention.

The cylindrical element 12 of this stent 10 includes double-curved portions (W) 21 located in the region of the valley where each interconnecting member 13 is connected to an adjacent cylindrical element 12. The peak portions (inverted-U) 22 and the valley portions (U) 23 also form the cylindrical element 12 of the stent 10. A shoulder region 24 extending from each valley portion to peak portion (inverted U) 22 allows the peak portion to be nested in a tight formation next to an adjacent cylindrical element 12. This shoulder region 24 provides a transition region between the peak portions (inverted U) 22 and the valley portions (U) 23 and double-curved portion (W) 21 to allow adjacent cylindrical elements to nest within one another and thereby better support the artery walls with smaller gaps between stent struts. In this manner, the shoulder region 24 provides more dense coverage of the serpentine pattern of the cylindrical element to create a fairly uniform strut pattern which fully supports the walls of the diseased artery. For this reason, there are no or few areas of the stent wall which do not have struts for supporting the wall of the artery. Each of the valley portions (U) 23 forms a Y-shaped member when connected to an interconnecting member 13. As can be seen in this particular design, each of the valley portions (W's and U's) 21 and 23 have an interconnecting member which connects that cylindrical element 12 to an adjacent cylindrical element. As a result, each cylindrical element 12 is connected to an adjacent cylindrical element by at least four interconnecting members 13. The peak portions (inverted "U") 22 are not directly connected to any adjacent cylindrical element to allow for radial expansion. The eight interconnecting members 13 which are connected to each cylindrical element 12 are discontinuous with each other to produce a highly flexible stent that does not kink upon bending. This particular design allows the stent 10 to be placed in tortuous anatomy, where the stent 10 will conform to the particular anatomy of the patient. For example, if the stent 10 is placed in a curved portion of an artery, then the flexibility of the stent will allow it to take on the same curved shape without kinking and will still be capable of fully supporting the artery. Additionally, the stent's resistance to kinking helps prevent occlusion of the vessel lumen by the stent struts. Even though the stent 10 is flexible, it is still rigid when collapsed so that it can be placed on the delivery catheter and moved into the desired location in the patient's vasculature.

The stent 10 also includes end rings 25 and 26 which comprise all "W" shaped portions 27 to provide additional strength to the ends of the stent 10. This "W" pattern also helps to increase the overall radiopacity of the stent by virtue of the additional material needed to create such a "W" pattern. As a result, the stent 10 should be easily observable by a physician using imaging instrumentation, such as a fluoroscope.

It should be appreciated that the present design can be made with a number of peaks and valleys, preferably ranging from 4 to 16. The number of peaks and valleys will depend upon the particular physical characteristics desired, along with the particular application to which the stent will be used.

While the stent design of the present invention has practical applications for procedures involving vessel diameters from about 3.0 to 14.0 millimeters, it should be appreciated that the stent pattern could also be successfully used in procedures involving larger lumens of the body. Due to the increase of the longitudinal flexibility provided by the present stent design, such applications could include larger diameter vessels where added flexibility in reaching the vessel is needed.

While FIGS. 1-3 illustrate one type of endoprosthesis, the general teachings thereof can be applied to other types of endoprostheses. This includes other types of stents that have different strut elements in different shapes and configurations. As such, FIGS. 1-3 are provided as an example of one type of endoprosthesis that can be coated with the polymer/drug of the present invention in order to achieve effective drug delivery into the lumen adjacent to the endoprosthesis.

The drug eluting endoprostheses of the present invention can be made of a variety of materials, such as, but not limited to, those materials which are well known in the art of endoprosthesis (e.g., stent) manufacturing. This can include, but is not limited to, an endoprosthesis body having a primary material. Alternatively, at least two of the annular elements or different portions can be made of different materials. Generally, the materials for the endoprosthesis can be selected according to the structural performance and biological characteristics that are desired.

In one configuration, the endoprothesis body has multiple layers, with at least one layer being applied to a primary material forming the annular elements. As such, at least one annular element can have multiple layers that are different from at least one other annular element. The multiple layers can be resiliently flexible materials or rigid and inflexible materials, and selected combinations thereof. For example, materials such as Ti3Al2.5V, Ti6Al4V, 3-2.5Ti, 6-4Ti and platinum may be particularly good choices for adhering to a flexible material, such as, but not limited to, Nitinol and providing good crack arresting properties. The use of resiliently flexible materials can provide force-absorbing characteristics to the structures, interconnectors, and/or other endoprosthesis components, which can also be beneficial for absorbing stress and strains, which may inhibit crack formation at high stress zones. Also, the multiple layers can be useful for applying radiopaque materials to selected annular elements, such as end annular elements to provide different characteristics. For example, types of materials that are used to make an endoprosthesis can be selected so that the endoprosthesis is capable of being collapsed during placement and expanded when deployed. Usually, the endoprosthesis can be self-expanding, balloon-expandable, or can use some other well-known configuration for deployment. Details of expandable stents can be found in U.S. Pat. No. 3,868,956 to Alfidi et al.; U.S. Pat. No. 4,512,338 to Balko et al.; U.S. Pat. No. 4,553,545 to Maas, et al.; U.S. Pat. No. 4,733,665 to Palmaz; U.S. Pat. No. 4,762,128 to Rosenbluth; U.S. Pat. No. 4,800,882 to Gianturco; U.S. Pat. No. 5,514,154 to Lau, et al.; U.S. Pat. No. 5,421,955 to Lau et al.; U.S. Pat. No. 5,603,721 to Lau et al.; U.S. Pat. No. 4,655,772 to Wallstent; U.S. Pat. No. 4,739,762 to Palmaz; and U.S. Pat. No. 5,569,295 to Lam.

Furthermore, details of self-expanding stents can be found in U.S. Pat. No. 4,580,568 to Gianturco; U.S. Pat. No. 4,830,003 to Wolff, et al.; U.S. patent application Ser. No. 10/158,362 to Denison; and U.S. Pat. Nos. 6,537,311 and 6,814,749 to Cox, et al.

Embodiments of the endoprosthesis body can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as Nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of an endoprosthesis can be of a NiTi alloy that forms superelastic Nitinol. In the present case, Nitinol materials can be trained to remember a certain shape, straightened in a shaft, catheter, or other tube, and then released from the catheter or tube to return to its trained shape. Also, additional materials can be added to the Nitinol depending on the desired characteristic. The alloy may be utilized having linear elastic properties or non-linear elastic properties.

An SMP is a shape-shifting plastic that can be fashioned into an endoprosthesis in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo(ε-caprolactone)diol, oligo(ρ-dioxanone)diol, and non-biodegradable polymers such as, polynorborene, polyisoprene, styrene, butadiene, polyurethane-based materials, vinyl acetate-polyester-based compounds, and others yet to be determined. As such, any SMP can be used in accordance with the present invention.

An endoprosthesis body having at least one layer made of an SMM or suitable superelastic material and other suitable layers can be compressed or restrained in its delivery configuration within a delivery device using a sheath or similar restraint, and then deployed to its desired configuration at a deployment site by removal of the restraint as is known in the art. An endoprosthesis body made of a thermally-sensitive material can be deployed by exposure of the endoprosthesis to a sufficient temperature to facilitate expansion as is known in the art.

Also, the endoprosthesis body can be comprised of a variety of known suitable deformable materials, including stainless steel, silver, platinum, tantalum, palladium, nickel, titanium, Nitinol, Nitinol having tertiary materials (U.S. 2005/0038500, which is incorporated herein in its entirety by reference), niobium-tantalum alloy optionally doped with a tertiary material (U.S. 2004/0158309, 2007/0276488, and U.S. Ser. No. 12/070,646, which are each incorporated herein by specific reference) cobalt-chromium alloys, or other known biocompatible materials. Such biocompatible materials can include a suitable biocompatible polymer in addition to or in place of a suitable metal. The polymeric endoprosthesis can include biodegradable or bioabsorbable materials, which can be either plastically deformable or capable of being set in the deployed configuration. If plastically deformable, the material can be selected to allow the endoprosthesis to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the required catalyst to set or cure the polymer.

In one embodiment, the stent or other medical device is made from a superelastic alloy such as nickel-titanium or Nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the Nitinol stent comparable to that of a stainless steel stent of the same size and strut pattern coated with a thin layer of gold. The Nitinol stent has improved radiopacity yet retains its superelastic and shape memory behavior and further maintains a thin strut/wall thickness for high flexibility.

Additional materials that can be used are described in U.S. Publication 2009/0093875, which is incorporated by reference herein in its entirety.

Moreover, the endoprosthesis body can include a radiopaque material to increase visibility during placement. Optionally, the radiopaque material can be a layer or coating any portion of the endoprosthesis. The radiopaque materials can be platinum, tungsten, silver, stainless steel, gold, tantalum, bismuth, barium sulfate, or a similar material.

The stents of the present invention can be made in many ways. However, the preferred method of making the stent is to cut a thin-walled tubular member, such as Nitinol tubing to remove portions of the tubing in the desired pattern for the stent, leaving relatively untouched the portions of the metallic tubing which are to form the stent. It is preferred to cut the tubing in the desired pattern by means of a machine-controlled laser.

A suitable composition of Nitinol used in the manufacture of a self-expanding stent of the present invention is approximately 55% nickel and 44.5% titanium (by weight) with trace amounts of other elements making up about 0.5% of the composition. The austenite transformation temperature is between about −15° C. and 30° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys, to obtain the same features of a self-expanding stent made in accordance with the present invention.

The stent of the present invention can be laser cut from a tube of super-elastic (sometimes called pseudo-elastic) nickel titanium (Nitinol) whose transformation temperature is below body temperature. All of the stent diameters can be cut with the same stent pattern, and the stent is expanded and heat treated to be stable at the desired final diameter. The heat treatment also controls the transformation temperature of the Nitinol such that the stent is super elastic at body temperature. The transformation temperature is at or below body temperature so that the stent will be superelastic at body temperature. The stent can be electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing of a self-expanding stent made in accordance with the present invention may be made of suitable biocompatible material besides super-elastic nickel-titanium (NiTi) alloys. In this case the stent would be formed full size but deformed (e.g. compressed) to a smaller diameter onto the balloon of the delivery catheter to facilitate intra luminal delivery to a desired intra luminal site. The stress induced by the deformation transforms the stent from an austenite phase to a martensite phase, and upon release of the force when the stent reaches the desired intra luminal location, allows the stent to expand due to the transformation back to the more stable austenite phase. Further details of how NiTi superelastic alloys operate can be found in U.S. Pat. Nos. 4,665,906 and 5,067,957 to Jervis, the entire disclosures of which are incorporated by reference herein.

The tubing also may be made of suitable biocompatible material such as stainless steel. The stainless steel tube may be alloy-type: 316L SS, Special Chemistry per ASTM F138-92 or ASTM F139-92 grade 2.

The stent diameters are very small, so the tubing from which it is made must necessarily also have a small diameter. For PTCA applications, typically the stent has an outer diameter on the order of about 1 mm (0.04-0.09 inches) in the unexpanded condition, the same outer diameter of the hypotubing from which it is made, and can be expanded to an outer diameter of 40 mm or more. The wall thickness of the tubing is about 0.076-0.381 mm (0.003-0.015 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

Coating Composition

In accordance with one embodiment of the invention, the stent is coated with at least one polymeric coating. Preferably, the coating functions as a drug delivery system that controls the release of the drug contained therein. Examples of such biocompatible polymeric materials can include a suitable hydrogel, hydrophilic polymer, hydrophobic polymers, bioabsorbable polymers, and monomers thereof. Examples of such polymers can include nylons, poly(alpha-hydroxy esters), polylactic acids, polylactides, poly-L-lactide, poly-L-lactide, poly-L-lactide-co-L-lactide, polyglycolic acids, polyglycolide, polylactic-co-glycolic acids, polyglycolide-co-lactide, polyglycolide-co-L-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, poly(ethylene-co-vinyl alcohol) (EVAL), poly(vinyl alcohol), poly(N-vinylpyrrolidone) (PVP), combinations thereof, polymers having monomers thereof, or the like. Additionally, the coating can include hydrophilic and/or hydrophobic compounds, polypeptides, proteins, amino acids, polyethylene glycols, parylene, heparin, phosphorylcholine, or the like. In accordance with a preferred embodiment, the polymeric coating includes poly(ethylene-co-vinyl alcohol) (EVAL).

Examples of solvents that can be used with EVAL include DMAC, DMSO, DMF, formamide, N-methyl-2-pyrrolidone (NMP), sulfolane, benzyl alcohol, cyclohexanol, phenol, formic acid, m-cresol, p-cresol, trifluoroacetic acid, glycerol, ethylene glycol, propylene glycol, and mixtures thereof.

The polymeric coating can contain a therapeutic agent. The coating facilitates the loading or delivery of the therapeutic agent. In accordance with a preferred embodiment, the therapeutic agent is a cytostatic agent. Some non-limiting examples of cytostatic therapeutic agents include marcrolide immunosuppressive, macrolide antibiotics, rapamycin, protaxel, taxanes, docetaxel, zotaroliums, novolimus, zotarolimus, everolimus, sirolimus, biolimus, myolimus, deforolimus, tacrolimus, or temsirolimus compounds, structural derivatives and functional analogues of rapamycin, structural derivatives and functional analogues of everolimus, structural derivatives and functional analogues of zotarolimus, sirolimus, biolimus, myolimus, deforolirnus, tacrolimus, or temsirolimus compounds.

Further examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastics and antimitotic. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, and dexamethasone For example and not limitation, the coating can include a therapeutic agent in addition to the cytostatic drug or instead of the cytostatic drug. In this regard, the therapeutic agent can include anti-proliferative, anti-inflammatory, antineoplastic, antiplatelet, anti-coagulant, anti-fibrin, antithrombotic, antimitotic, antibiotic, antiallergic and antioxidant compounds, HMG-CoA reductase inhibitors, and peroxisome proliferator-activated receptor α (PPAR α) agonists such as fenofibrates (clofibrate, ciprofibrate, benzafibrate, and Tricor and Trilipix ABT-335). Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

In accordance with a preferred embodiment of the invention, the drug eluting stent is self-expanding. In accordance with a preferred embodiment, the stent can have a structural body that is prepared from a superelastic material that has shape memory, such as Nitinol or the like. The structural body can be coated with at least one polymeric coating, such as poly(ethylene-co-vinyl alcohol) (i.e., EVAL), that functions as a drug delivery system that controls the release of drug contained therein. The drug contained within the polymer coating can be a cytostatic drug, an anti-retinoic drug (e.g., rapamycin, everolimus, analogs thereof, and the like) or other drug useful for inhibiting cell proliferation within the vascular lumen. The drug can be any drug having a therapeutic benefit for treating and/or preventing a disease or condition. The polymer coating that contains the drug can also be coated by another layer of the same or different polymer that further controls the drug release profile from the stent.

In one embodiment, the stent of the present invention is an everolimus-eluting self-expanding Nitinol stent with a elution rate-controlling polymeric coating prepared from poly (ethylene-co-vinyl alcohol). The stent was designed to address and overcome three potential shortcomings of prior self-expanding drug eluting stent (DES), namely (1) inadequate drug delivery to the target tissue, (2) short profiles of elution leading to transiently high systemic drug concentrations, and (3) a tendency towards strut fracture when implanted into the SFA.

In one embodiment, a coated stent can be loaded with a relatively high overall drug content (e.g., 225 μg everolimus/$cm^2$ stent area) as compared to other coronary stents that elute other drugs (e.g., 140 μg sirolimus/$cm^2$ or 160 μg zotarolimus/$cm^2$). Everolimus effectively inhibits neointiraal hyperplasia in animal models and, when formulated onto coronary stents at a dose of 150 μg everolimus/$cm^2$ stent area, it reduces restenosis as compared to bare metal or paclitaxel-eluting stents. The dosage of 225 μg everolimus/$cm^2$ stent area is an exemplary dose for the drug eluting stent embodiment as this dose roughly represents a 2:1 increase in dose/$mm^2$ arterial area as compared to the coronary DES formulation.

In one embodiment, the drug eluting stent in accordance with the present invention is characterized as follows: a structural body made of Nitinol or other similar superelastic alloy; having a maximum diameter when expanded of 3 mm to about 20 mm, more preferably from about 3.5 mm to about 15 mm, and most preferably from about 4 mm to about 12 mm; having a minimum inner diameter when in a deployable of 0 μm (i.e., touching) to about 1000 μm, more preferably from about 0 μm to about 500 μm, and most preferably from about 0 um to about 200 μm; and having a polymeric coating of poly(ethylene-co-vinyl alcohol) at a thickness of about 2 μm to about 50 μm, more preferably from about 4 μm to about 25 μm, even more preferably from about 5 μm to about 20 μm, and most preferably from about 13 to about 15 μm.

In one embodiment, the stent has an unconstrained, nominal diameter of 5 mm, 6 mm, 7 mm or 8 mm. Representative lengths for each diameter are 28 mm, 30 mm, 40 mm, 60 mm, 80 mm, or 100 mm, 120 mm, 150 mm, or 200 mm long. In some embodiments, each of the above lengths may vary by about ±4.0 mm.

Equally important as the total bulk dose of everolimus contained on the stent is its kinetic release profile. Using an EVAL (i.e., poly(ethylene-co-vinyl alcohol)) system, the everolimus eluting stent embodiment was designed to release drug over a longer period of time as compared to coronary stents. In a broad sense, a coronary DES, as opposed to a periphery DES, releases drugs over about 30 days. In this embodiment, the everolimus eluting stent embodiment can release everolimus more slowly, and thereby eluting approximately 80% of its drug load over the first days 90 days.

The relatively high drug load and slow release profile of the everolimus-eluting stent of the present invention can assure that the vessel walls of treated peripheral target arteries will contain more everolimus for longer periods of time compared to coronary arteries treated with coronary DES.

A second salient feature of the slow drug release of the everolimus-eluting stent with the poly(ethylene-co-vinyl alcohol) coating embodiment is that the potential for systemic everolimus overexposure is minimized.

In one embodiment, the present invention utilizes a well-characterized Nitinol stent. As a result, there are ample in vitro and clinical data to suggest that the stent is able to withstand the chronic mechanical forces inherent to the SFA. For example, in a comparative retrospective study of three different peripheral stents, radiographic strut fracture within the Nitinol stent was observed in only 1.8% of cases after a mean follow-up of 15±9 months. However, fractures of some Nitinol stents were observed in 28% after a mean follow-up of 32±16 months, and 19% after a mean follow-up of 43±24 months. Similarly, in a randomized, prospective, single-center study of percutaneous transluminal angioplasty (PTA) alone versus PTA with the Nitinol stent embodiment, the Nitinol stent fracture was observed in only 2% of patients. Finally, in a multicenter single-arm prospective registry, strut fracture of the Nitinol stent embodiment was observed in 2.1% (3/143) stents after one year. Taken together, the results of these three studies suggest that the Nitinol stent is well-suited to the environment of the SFA, and that chronic implantation is not associated with high rates of fracture. A Nitinol stent can be configured to include a polymer having a drug so as to be a drug eluting stent in accordance with the present invention.

In one embodiment, the present invention includes an everolimus-eluting, self-expanding Nitinol stent. Such a stent can be used to inhibit restenosis after endovascular intervention in the SFA by selectively eluting everolimus into the vasculature tissue in an amount significantly higher than systemic elution into the bloodstream. As provided herein, there is ample in vitro, in vivo, experimental, and clinical evidence to suggest that the everolimus-eluting, self-expanding Nitinol stent (1) delivers a relatively high concentration of everolimus to the target vascular tissue over a prolonged therapeutic interval, (2) minimizes potential systemic exposure to everolimus through a slow systemic (e.g., blood) release profile, and (3) can withstand and adapt to the rigorous mechanical environment of the SFA.

In one aspect, the polymeric coatings can cooperate so as to control elution of the drug from the stent. This can include facilitating elution into the tissue adjacent to the stent and inhibiting elution into the bloodstream, thereby inhibiting systemic drug. The controlled elution can be accomplished by the coatings and artery tissues establishing a diffusion pathway having a steep concentration gradient with respect to the drug so as to induce the drug to diffuse through the diffusion pathway. The steep concentration gradient is accomplished by the coatings having a high concentration of drug and the tissue having a low concentration of drug, which thereby promotes diffusion through the diffusion pathway. Also, the coatings, drug, and tissue can provide lipophilic and/or hydrophilic diffusion pathways with the tissue being a sink to promote diffusion of the drug into the tissue.

Additionally, the diffusion pathway into the vascular tissue can be enhanced by the stent being placed in a blood vessel that passes blood. Blood, while containing some lipid-based components, is significantly more aqueous that than lipidic because the blood includes a significant amount of water. As such, a lipophilic drug will preferentially diffuse through a lipophilic diffusion pathway over an aqueous pathway. The lipophilic drug preferentially diffusing through the lipophilic diffusion pathway into the tissue adjacent to the stent over diffusion into the blood attributes to the vascular tissue adjacent to the stent obtaining a therapeutic concentration of drug and the system concentration being significantly below a therapeutic concentration and toxic concentration. Accordingly, systemic effects of the drug can be inhibited by maintaining an extremely low systemic drug concentration, thereby inhibiting the adverse effects of prolonged systemic drug. This can also be accomplished with hydrophilic and/or amphiphilic drugs and polymer components because tissues inherently have water as a major component.

In one embodiment, the coating/drug combination is configured to provide an extended elution profile that can elute substantially constant levels of drug over 3 months, more preferably over 6 months, and most preferably over 9 months. The slow elution kinetics attribute to the significantly inhibited systemic elution of the drug and helps to maintain the systemic of the drug below any therapeutic and/or toxic index. Additionally, the slow elution kinetics attributes to the drug preferentially diffusing through the lipophilic diffusion pathway because slow elution kinetics further drive the lipophilic drug through a lipophilic diffusion pathway over diffusing into the blood. Also, the slow elution kinetics can enable the tissue to retain sink-like properties with respect to the drug so as to provide a continuously steep concentration gradient through the lipophilic diffusion pathway.

In embodiments of the present invention that include self-expanding stents, the stent continually applies pressure to the vascular tissue. This continual application of pressure can cause the tissue to form troughs that receive the stent elements therein so that the contact area between the tissue and the stent is increased. Also, it is possible that such continuous pressure actually facilitates preferential diffusion of the drug through the lipophilic diffusion pathway. This can occur by the pressure shortening the diffusion pathway between the stent and the tissue by compression of the lipid membranes and/or compression of the coating layers.

It is thought, without being bound thereto, that the coating/drug combination that provides preferential diffusion of the drug through the lipophilic diffusion pathway over diffusion into the systemic blood supply cooperates with natural physiological processes in order to further differentiate the amount of drug in the vascular tissue adjacent to the sent compared to systemic drug. The difference in drug diffusion pathways that result in extremely low systemic concentrations is supplemented by the physiological functions of drug metabolism. Drug metabolism occurs mainly in organs that are removed from the vascular tissue, and preferentially not in the vascular tissue. This physiological process naturally further reduces the systemic concentration of drug without reducing the concentration of drug in the vascular tissue.

In one embodiment, the polymer/drug combination that is configured for prolonged elution can also allow for a substantially greater amount of drug loading on the stent. Some previously used stents with low drug loading concentrations have caused higher systemic drug concentrations. Now, the polymer/drug combination of the present invention can allow for substantially increased drug loading on the stent with reduced systemic concentrations. For example, the present invention can have a drug loading preferably greater than or equal to about 150 µg/cm$^2$, more preferably greater than or equal to about 200 µg/cm$^2$, and most preferably greater than or equal to about 225 µg/cm$^2$.

Similarly, the stents of the present invention can have substantially more total drug per stent than the stents that produce excessive systemic drug concentrations. For example, stents that produce excessive systemic concentrations of drug have had relatively lower amounts of total drug. However, the polymer/drug combination of the present invention can allow for the stents to have a substantially higher amount of total drug loading. Additionally, the stents of the present invention can have substantially more drug per area of artery into which the drug is to diffuse compared to prior stents.

In one embodiment, the polymeric coating can have a thickness of about 2 µm to about 50 µm, more preferably from about 4 µm to about 25 µm, even more preferably from about 5 µm to about 20 µm, and most preferably from about 13 µm to about 15 µm. The coating can be uniform or divided into discrete layers. The coating may have a primer layer of the same or different polymer, or no primer layer.

In one embodiment, the polymeric coating can have a primer coating against the metal, a drug-loaded coating disposed on the primer coating, and a topcoat disposed on the drug-loaded coating. This can include the primer coating being from about 1% to about 20% of the total coating thickness, more preferably from about 3% to about 15% of the total coating thickness, even more preferably from about 5% to about 10% of the total coating thickness, and most preferably about 7% of the total coating thickness. This can also include the drug-loaded coating being from about 25% to about 90% of the total coating thickness, more preferably from about 40% to about 80% of the total coating thickness, even more preferably about 50% to about 70% of the total coating thickness, even more preferably about 60%, and most preferably about 63% of the total coating thickness. Additionally, this includes the topcoat being from about 5% to about 50% of the total coating thickness, more preferably from about 15% to about 40% of the total coating thickness, more preferably from about 25% to about 35% of the total coating thickness, and most preferably about 30% of the total coating thickness.

In accordance with a further embodiment, the everolimus coated drug eluting stent mounted on a balloon catheter apparatus produces a pharmacokinetic profile that provides the therapeutic agent to the vasculature or target tissue in a sufficient and effective concentration. Indeed, the resulting pK profile or decline in tissue concentration with time can provide the therapeutic agent at a concentration necessary to prevent or inhibit restenosis. Pharmacokinetics includes the study of the mechanisms of absorption and distribution of an administered drug, the rate at which a drug action begins and the duration of the effect, the chemical changes of the substance in the body (e.g. by enzymes) and the effects and routes of excretion of the metabolites of the drug. Pharmacokinetic analysis is performed by noncompartmental (model independent) or compartmental methods. Noncompartmental methods estimate the exposure to a drug by estimating the area under the curve of a concentration-time graph. Compartmental methods estimate the concentration-time graph using kinetic models. Compartment-free methods are often more versatile in that they do not assume any specific compartmental model and produce accurate results also acceptable for bioequivalence studies.

Coating Procedure

In accordance with the invention, after the stent is formed according to methods and techniques described above, a polymer coating and therapeutic agent can be applied thereto. Some of the methods for coating stents with polymers includes dipping, spraying, inkjetting, painting, brushing, rolling, or otherwise depositing the polymeric coating on the endoprosthesis body. This can include such processes for one or more concentric layers of polymeric coating materials.

In one embodiment, the drug is mixed into a polymeric solution that is applied to the endoprosthesis by an acceptable method of application. Alternatively, a first layer of polymer can be applied to the stent and then a drug layer can be applied thereto with a topcoat of polymer being applied over the drug layer. In another alternative, a coated stent can be dipped into a drug solution so that the drug diffuses into the polymeric coating to achieve the desired amount of drug. In yet another alternative, a bare endoprosthesis can have a layer of drug applied thereto with at least one layer of polymer applied thereto.

After application of a fluid or gelatinous coating, the endoprosthesis can be dried so that the coating can be substantially solidified. Such drying can accomplished by passive or active drying. Passive drying includes retaining the coated stent in normal or ambient conditions so that a natural drying process occurs. Active drying includes the use of heat or forced air to cause the solvent in the liquid coating to evaporate from the coating, and thereby harden the coating so as to be substantially solid.

A specific process for coating a cytostatic therapeutic agent in a polymer, preferably in a poly(ethylene-co-vinyl alcohol), such as EVOH, provides for adequate coating integrity and release rate profiles. The manufacturing process for coating a cytostatic drug in EVAL polymer onto a stent is illustrated in FIGS. 4A and 4B.

Figure 4A:
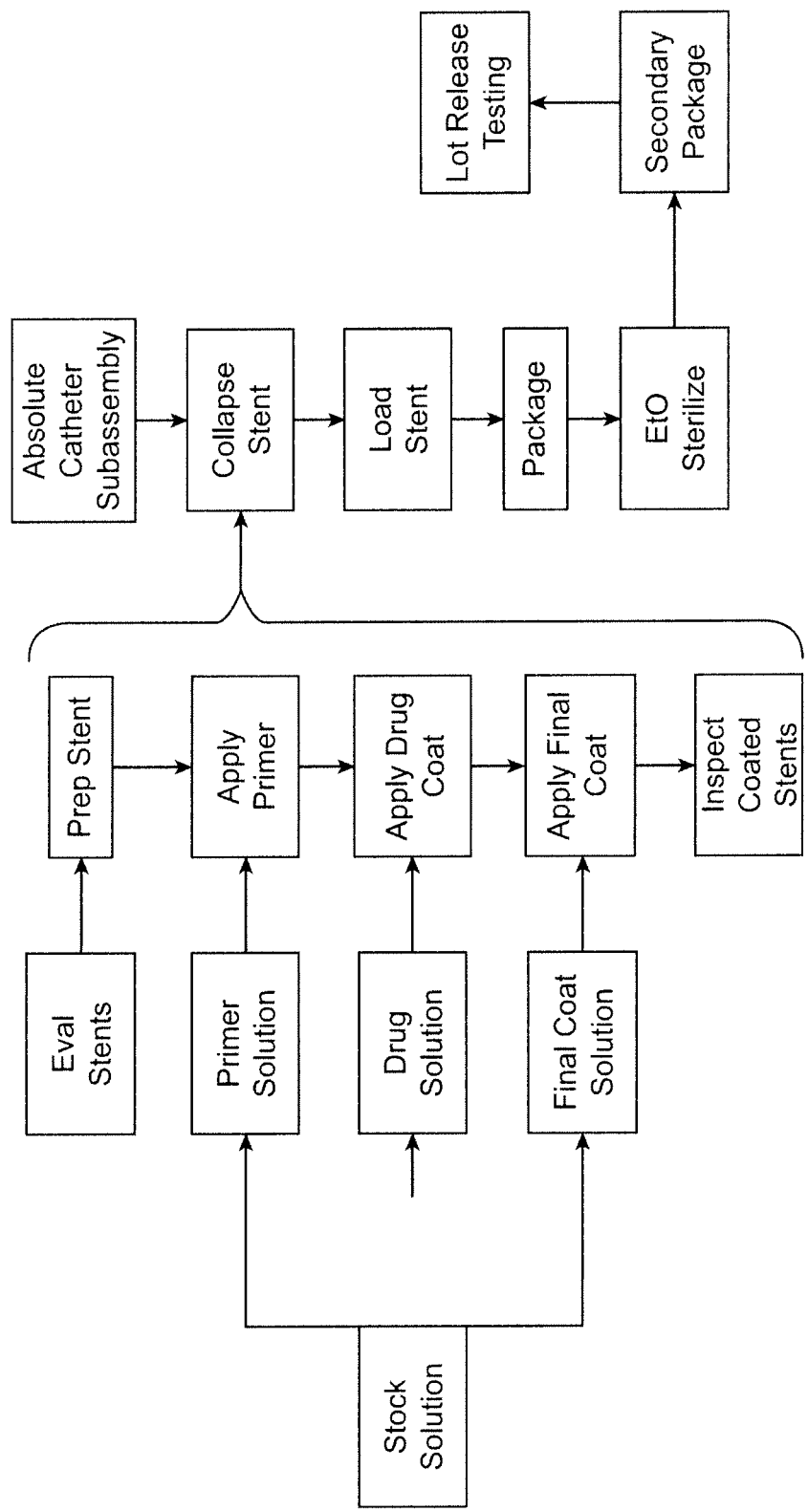
FIGS. 4A and 4B are process flow diagrams illustrating the manufacturing process for coating drugs in a polymer matrix onto a stent in accordance with the present invention.
Figure 4B:
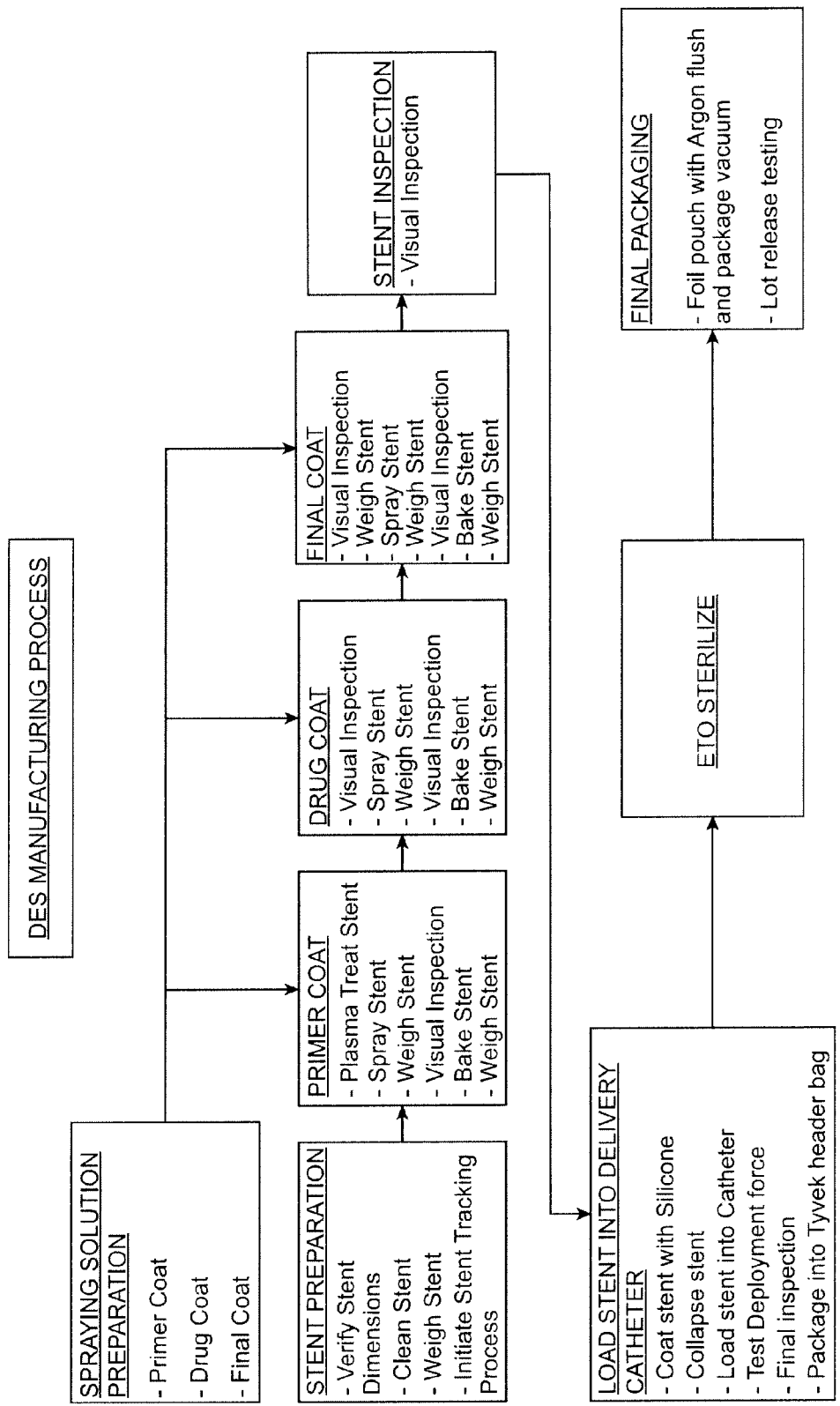

As illustrated in FIGS. 4A and 4B, the process steps include preparing the stent and preparing the spraying solutions to be used. Next, an optional primer is applied, the drug/polymer coating is applied and the final coating applied. Following the coating process, the stents are visually inspected to confirm that there are no defects. The acceptable stents are then collapsed, loaded onto a delivery catheter, packaged, sterilized and packaged into a secondary package for lot releasing testing.

Details of the process steps will be described herein. During stent preparation, the dimensions of the stent are measured to verify that it is within required tolerances. The stent is then ultrasonically cleaned in sterile water, ultrasonically cleaned in 70/30 isopropyl alcohol and room air dried. The stent is then weighed on a micro balance to establish an initial uncoated stent weight. The coating amount (coating thickness, drug amount) has been correlated with coating weight gain so that the change in stent weight as the stent is coated and baked is tracked throughout the manufacturing process. Following weighing of the stent, the stent is subjected to an argon gas plasma discharge under vacuum to prepare the surface for maximum polymer adhesion.

In one embodiment the stent is weighed using a microbalance made by modifying a Mettler-Toledo UMX2 Microbalance available from Mettler-Toledo International Inc. (Columbus, Ohio). The modified microbalance has a horizontal balance weighing pan and a stent lifter to facilitate loading the stent on the balance. As seen in FIGS. 5A and 5B, the microbalance has an enclosure 64 with an enclosure lid 63 and a stent lifter 61 which allows the stent 60 to be easily loaded onto the weighing pan 62. FIG. 5A shows the microbalance in the loading position, and FIG. 5B shows the microbalance in the weighing position with the enclosure lid 63 closed.

In an embodiment, the poly(ethylene-co-vinyl alcohol) may be purified by processing the typically available pellet form (available from Aldrich Chemicals) into a powder. The resulting material has more consistent and reproducible properties. The purifying procedure removes impurities, obtains desired molecular weight distribution, and achieves faster process time (fast solubility in solvents), thereby reducing the time when using the material in manufacturing. The molecular weight distribution may be more consistent because smaller molecular fragments are removed/reduced. A resulting coating may have a more predictable and less variable drug release properties.

In an example of the purification procedure for the poly (ethylene-co-vinyl alcohol), although the procedure may be applied to other polymers, a 10% by weight stock solution was prepared by dissolving the stock polymer into >99% N,N-dimethyl acetamide (Aldrich #271012-2L). Chilling the dimethyl acetamide solution of the polymer and adding cyclohexane drop wise produced a gel-like mass, swollen by solvent. The supernatant was pipetted off and the polymer gel was re-dissolved in N,N-dimethyl acetamide. The solution was then added to 100 ml of ethanol drop wise with vigorous mixing. After the addition was completed, the solution was allowed to stand at room temperature overnight. Then the solution was filtered off the white solid and the white solid was washed with cyclohexane overnight. The solution was again filtered off of the washed solid and dried to produce a fine, free flowing powder. The process above may be used with different solvent/polymer combinations to achieve similar results. In one embodiment, the ultimate precipitate In accordance with another embodiment, the EVAL purification process involves multiple washes of EVAL pellets with Ethanol at 59° C. A mixture of EVAL/Ethanol at 1:7 ratio (w/w) is heated in a flask at 59° C. with continuous stirring for approximately 24 hours. The flask is built with a jacket to circulate heated water to maintain the temperature of the EVAL/ethanol mixture at 59° C. At the end of the 24 hr period, the ethanol is drained out, EVAL pellets are rinsed with fresh ethanol and the wash cycle is repeated with fresh ethanol for a total of 4 washes. At the end of fourth wash cycle, the ethanol is collected and the EVAL pellets are vacuum dried at 120° C. Both EVAL and the last ethanol rinse are tested for total volatiles using thermogravimetric analysis, impurities in the final rinse using Fourier transform infrared spectroscopy, and metal impurities using an inductively coupled plasma (ICP) analysis for Mg, Pb, Ni, Hg, Al, K, P, and Na. The purified EVAL is stored in wide mouth type 3 soda lime glass ultra clean bottles with Teflon PTFE lined closures.

In an embodiment, preparation of a primer/topcoat polymer solution and drug/polymer solution starts with a stock solution of EVAL in DMA. Purified EVAL pellets and DMA are weighed into a type 3 soda lime ultra clean clear glass bottle to give 1:9 (w/w) EVAL/DMA ratio; the bottle is then capped with a Teflon PTFE lined closure. The mixture is heated in an oven at 80° C. for approximately 1.5 hours with continuous stirring. Heating is used to help dissolve the EVAL in DMA. The EVAL stock solution is stored at ambient temperature for a minimum six hours before using it for the preparation of coating solutions as described below. Typically the stock solution is used within 6 to 48 hours.

In a further embodiment, to prepare the primer/topcoat solution of EVAL, the stock solution of EVAL (10% EVAL in DMA) prepared as above is diluted with DMA to obtain 4.5% (w/w) EVAL in DMA. This may be achieved by weighing an appropriate amount of EVAL stock solution and DMA into an ultra clean type 3 soda lime clear glass bottle and stirring for approximately 10 minutes with a magnetic stirrer. For example, to prepare 100 g of primer/topcoat solution, 45 g of EVAL stock solution is mixed with 55 g of DMA. The solution may be stored at ambient temperature. Shelf life is typically about 2 weeks, but may be extended if the solution is refrigerated.

In another embodiment, the preparation of the drug/polymer solution comprises weighing a desired amount of Everolimus drug substance, EVAL stock solution, and DMA solvent into a type 3 soda lime ultra clean amber glass bottle to give 1:1.6 ratio of drug/polymer in the mixture. The mixture is then stirred with a magnetic stirrer for approximately 10 minutes. Depending on the amount of solution desired, the amount of each component may be varied. Drug/polymer solutions may be stored at ambient temperature. Shelf life is typically about 2 weeks at ambient temperature, but may be extended if the solution is refrigerated.

In accordance with one embodiment, the stent is initially coated with a primer coating consisting of a poly(ethylene-co-vinyl alcohol) in dimethylacetamide (DMA) solvent. The coating process includes rotating a stent on a spraying mandrel and passing the rotating stent under the spray nozzle for the length of the stent, for one pass. The stent is then passed under the spray nozzle in the opposite direction for the length of the stent for another pass. Following the second pass, the stent is moved to a drying station where the stent is dried, for example, by passing hot nitrogen gas over and through the rotating stent. The stent can be sprayed with several cycles, each cycle including two spray passes and a drying step. In accordance with an embodiment, the cycles can range from 1 to 10 cycles, preferably, 2-4 cycles. A summary of machine settings and minimum to maximum settings for applying the primer polymer coating is disclosed in Table A.

TABLE A

Settings for Spraying Stent with Primer Polymer Coat

| Machine Settings | Normal Settings | Min. to Max. Settings |
| --- | --- | --- |
| Stent rotation (RPM) | 100 | 50-250 |
| Stent linear speed (mm/sec) | 6 | 2-20 |
| Drying Temperature at Stent (° C.) | 50 | 30-100 |
| Drying time (sec) | 20 | 5-60 |
| Number of spray passes/cycle | 2 | 1-10 |
| Number of cycles | 3 | 1-10 |
| Start Position (mm) | 40 | 10-60 |
| Spray Length (mm) | Adjusted per stent length | 10-120 |

Following the spraying step, the stent is weighed to determine the weight of the primer coating. This weight can be used to adjust spraying rates. The stent is then inspected to ensures that there are no coating defects. All acceptable stents are then baked to remove excess solvent. The temperature at which the stent bakes ranges from 50 to 180° C., preferably from 130 to 150° C. The stent is baked for 5-120 minutes, preferably from 40-80 minutes. Following baking, the stent is then weighed to determine the primer coated stent weight gain. The stent is then placed in a sealed glass vial to control the stent's environment.

In accordance with an alternative embodiment, therapeutic agent can also be added to the primer coating.

Following the primer coating, the stent is coated with the therapeutic agent coating. In accordance with a preferred embodiment, the stent is coated with a drug coating consisting of therapeutic agent, (e.g., everolimus), in an EVAL copolymer matrix with a DMA solvent. Prior to mounting the stent having the primer coat thereon, the stent is visually inspected. The stent is then loaded and rotated on a spraying mandrel. The coating process includes rotating a stent on a spraying mandrel and passing the rotating stent under the spray nozzle for the length of the stent, for one pass. The stent is then passed under the spray nozzle in the opposite direction for the length of the stent for another pass. Following the second pass, the stent is moved to a drying station where the stent is dried, for example, by passing hot nitrogen gas over and through the rotating stent. The stent can be sprayed with several cycles, each cycle including two spray passes and a drying step. In accordance with a preferred embodiment, the cycles can range from 1 to 50 cycles, preferably, 20-40 cycles. A summary of machine settings and minimum to maximum settings for applying the drug coating is disclosed in Table B.

TABLE B

Settings for Spraying Scent with Drug Coating

| Machine Settings | Normal Settings | Min. to Max. Settings |
| --- | --- | --- |
| Stent rotation (RPM) | 100 | 50-250 |
| Stent linear speed (mm/sec) | 6 | 2-20 |
| Drying Temperature at Stent (° C.) | 50 | 30-100 |
| Drying time (sec) | 20 | 5-60 |
| Number of spray passes/cycle | 2 | 1-10 |
| Number of cycles | 27 | 1-50 |
| Start Position (mm) | 40 | 10-60 |
| Spray Length (mm) | Adjusted per stent length | 10-120 |

Following the spraying step, the stent is weighed to determine the weight of the drug coating. This weight can be used to adjust spraying rates. The stent is then inspected to ensure that there are no coating defects. All acceptable stents are then baked to remove excess solvent. The temperature at which the stent bakes ranges from 50 to 180° C., preferably from 60 to 80° C. The stent is baked for 5-120 minutes, preferably from 20-40 minutes. Following baking, the stent is then weighed to determine the drug coated stent weight gain. The stent is then placed in a sealed glass vial to control the stent's environment.

Following applications of the primer coating and the drug coating, the stent is coated with a final coat of polymer. In accordance with a preferred embodiment, the final coating consists of an EVAL copolymer in a DMA solvent. Prior to mounting the stent having a primer coating and a drug coating, the stent is visually inspected and, in accordance with a preferred embodiment, also weighed. The stent is then loaded and rotated on a spraying mandrel. The coating process includes rotating a stent on a spraying mandrel and passing the rotating stent under the spray nozzle for the length of the stent, for one pass. The stent is then passed under the spray nozzle for the opposite direction for the length of the stent for another pass. Following the second pass, the stent is moved to a drying station where the stent is dried, for example, by passing hot nitrogen gas over and through the rotating stent. The stent can be sprayed with several cycles, each cycle including two spray passes and a drying step. In accordance with a preferred embodiment, the cycles can range from 1 to 50 cycles, preferably, 10 to 20 cycles. A summary of machine settings and minimum to maximum settings for applying the final coating to the stent is disclosed in Table C.

TABLE C

Settings for Spraying Stent with Final Polymer Coating

| Machine Settings | Normal Settings | Min. to Max. Settings |
| --- | --- | --- |
| Stent rotation (RPM) | 100 | 50-250 |
| Stent linear speed (mm/sec) | 6 | 2-20 |
| Drying Temperature at Stent (° C.) | 50 | 30-100 |
| Drying time (sec) | 20 | 5-60 |
| Number of spray passes/cycle | 2 | 1-10 |
| Number of cycles | 14 | 1-50 |
| Start Position (mm) | 40 | 10-60 |
| Spray Length (mm) | Adjusted per stent length | 10-120 |

Following the spraying step, the stent is weighed to determine the final coating weight gain. This weight can be used to adjust spraying rates and for process control. The stent is then inspected to ensure that there are no coating defects. All acceptable stents are then baked to remove excess solvent. The temperature at which the stent bakes ranges from 50 to 180° C., preferably from 70 to 90° C. The stent is baked for 5-120 minutes, preferably from 20-40 minutes. Following baking, the stent is then weighed to determine the final coat weight gain. The stent is then placed in a sealed glass vial to control the stent's environment.

Figure 6:
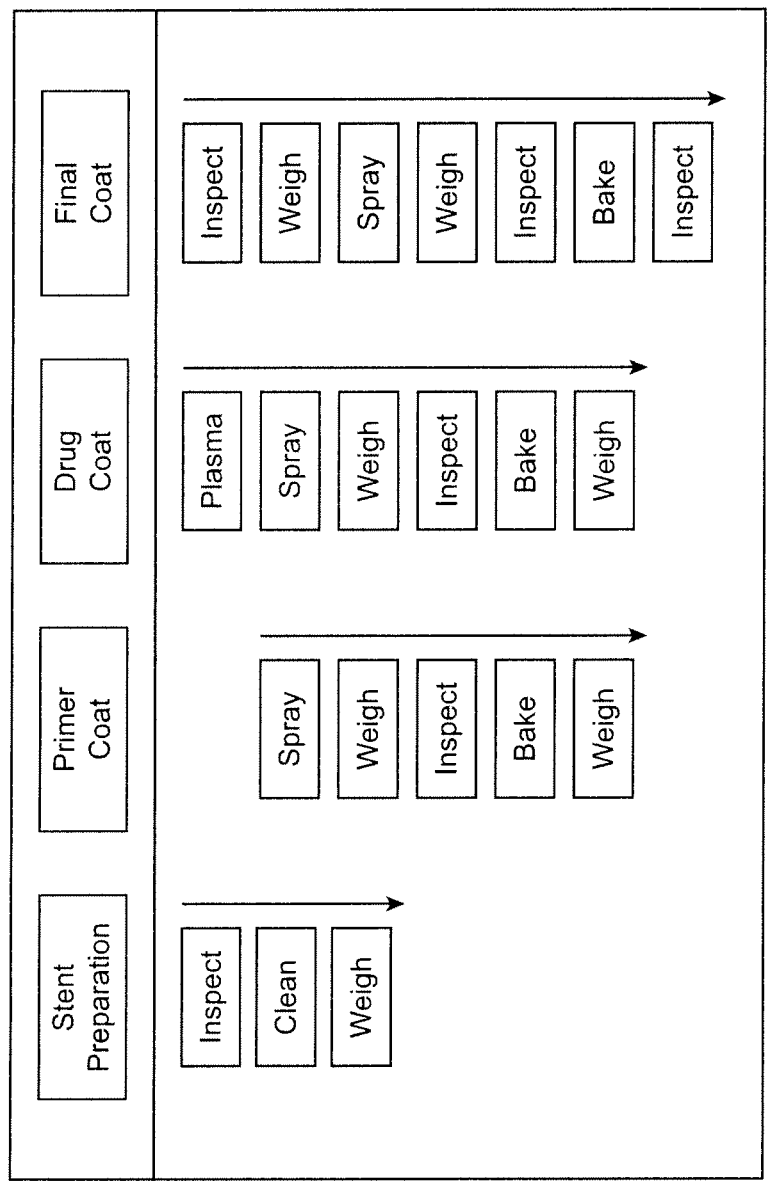
FIG. 6 is a flow chart illustrating a stent spraying process according to an embodiment of the present invention.

In accordance with an alternative embodiment, the primer coating can be eliminated from the manufacturing steps. The typical purpose of a primer coat is to enhance adhesion between the metal stent and the drug coating. As seen FIG. 6, the typical stent spraying process may have a significant reduction in the number of manufacturing steps if the primer coat is removed. Primer removal provides a simpler design, reduces the amount of implanted EVAL polymer into a patient, and enhances manufacturing.

Figure 7:
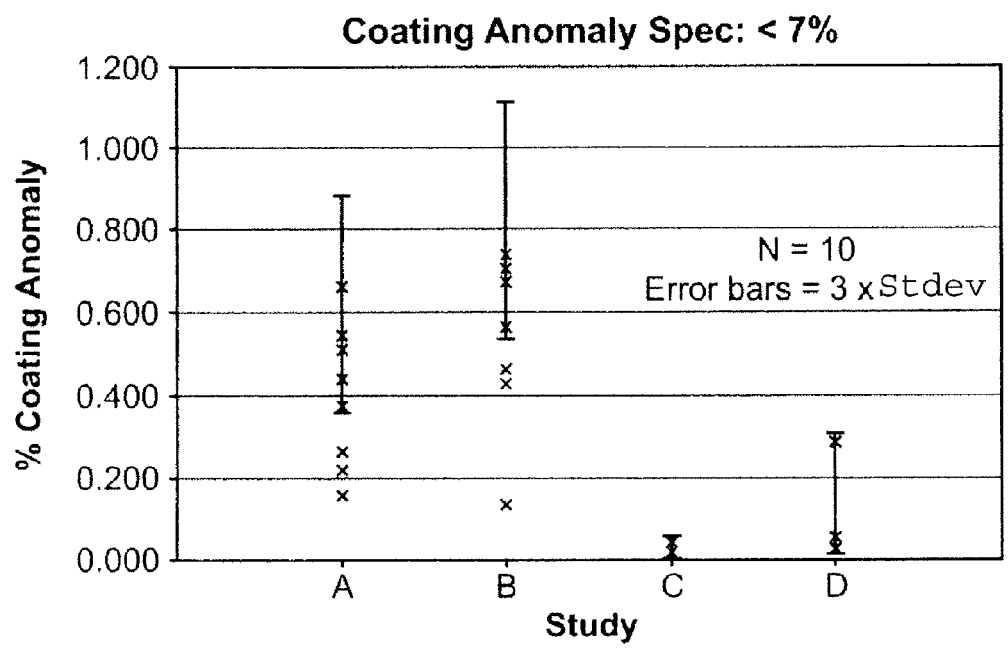
FIG. 7 is a graph illustrating the coating anomalies in stents with and without primer coats.

A measure of the adhesion of the drug coating to the metal stent is represented by the coating integrity. A coating integrity test measures the coating anomalies, or area of damaged coating after a stent has been deployed from a catheter and expresses this damages as a % of the total stent surface area. Typically, the drug release of the DES is not significantly affected when the coating anomaly is <7%. The graph in FIG. 7 shows that stents with a primer and stents without a primer have similar coating anomalies, and are both below the typical specification requirement of <7%. Each Study had 10 samples, with Study A and Study B having a primer coat, and Study C and Study D not having a primer coat. Further testing of drug release rate, drug total content, and impurity content has shown no significant impact from primer coat removal.

In accordance with an alternative embodiment, the primer coating and/or the final polymer coating can be eliminated from the manufacturing steps. Furthermore, although the preferred process includes spraying of the primer, drug and final coatings, the coatings can also be applied by dipping, painting, droplet, or continuous bead methods, and plasma deposition, as known to those skilled in the art. In yet another alternative, the weighing step after the baking step can also be eliminated by validating the with loss through the baking process. Alternatively, the weighing step after the spraying step can be eliminated by validating the consistency of the spraying process. In yet another alternative, a vacuum oven is used to remove solvent instead of ovens discussed above.

Following application of the final coating, the stents can be loaded onto the delivery system. Prior to initiating the loading process, the stent is visually inspected. The stent is then coated with silicone medical fluid lubricant to reduce friction and possible damage in subsequent steps. The stent is cooled, collapsed to the delivery system diameter, and then transferred into a collapse sheath. This sheath holds the stent in the collapsed state until it is loaded into the delivery system. The stent is pushed from the collapse sheath and loaded onto the delivery catheter. The deployment force is then tested by applying a measured force to the delivery system to move the stent a few millimeters. The force to move the stent must be within a specified limit. Following the testing of the deployment force, the stent is pushed back to its fully loaded position. The assembled stent/catheter product is measured, tested and visually inspected for correct assembly. The final produce is placed in a protective coil and is sealed inside a sterile barrier Tyvek header bag. Subsequently, the product is sterilized, preferably subjected to Eta sterilization, and returned for final packaging. The sterilized header bag is placed into a foil pouch, the pouch is evacuated and then filled with argon gas to protect the drug product from light, moisture and oxygen.

Alternative Coating Fabrication

Some drug eluting stent manufacturing processes require the removal of solvents that have a high boiling point. Solvent removal for certain polymer/solvent combinations cannot be fully removed by dry baking alone. The dry baking occurs after the application of the drug coat and then again after the application of a final coat. A humidity bake process may be used to minimize the amount of solvent remaining inside of the coated layers after the completion of the spray coating and dry baking of the stents. If humidity is added to the dry baking processes, then the separate humidity bake step at the end may be eliminated.

To fabricate a stent coating, for example, a polymer can be dissolved in a solvent or in a system comprising a mixture of solvents to form the polymer solution. One example of a suitable polymer is poly(ethylene-co-vinyl alcohol) (EVAL). The polymer solution can then be applied onto the surface of the stent by a conventional method, e.g., by spraying or dipping, to form the coating. In one embodiment, the solvent can have boiling point greater than about 120° C., for example, above about 130° C. at atmospheric pressure. In another embodiment, the solvent can have vapor pressure at 20° C. of less than about 15 Torr, for example, below about 10 Torr. In yet another embodiment, the solvent can have both boiling point and vapor pressure described above.

In an embodiment, the concentration of EVAL in the polymer solution can be between about 1 and 5 mass %, for example, about 2 mass %. An EVAL solution can be prepared by combining EVAL with a solvent or a mixture of solvents described above and by stirring the composition for about 2 to 4 hours at a temperature between about 75° C. and about 85° C., for example, about 80° C. EVAL can be used to manufacture of the primer layer, drug-polymer layer, and/or the topcoat layer.

According to embodiments of the present invention, the coating can be baked in an oven at an elevated temperature, while the oven environment has a high relative humidity. The baking temperature can be within a range of between about 30° C. and about 110° C., for example, about 80° C.

The high humidity atmosphere can be created in the baking oven, for example, by having a tray or pan of water inside the oven, spraying or misting water inside the oven, or passing into the oven a water fog or mist that is generated outside the oven. The elevated humidity can be created during, and/or prior to, the baking process. The relative humidity of the oven environment where the stent coating is baked can be within a range of between about 20% and about 100%, preferably about 40% to 80%, for example about 60%, or in another example about 80%. In another embodiment, the relative humidity is about 40% to about 100%, preferably about 60% to about 100%, and more preferably about 60% to about 80%. The baking time can be between about 10 minutes and about 240 minutes, for example, about 30 minutes. Among other benefits, the method of forming the stent coating according to embodiments of the present invention allows for faster drying time without substantial increase in the baking temperature. It is believed that this process will facilitate acceptable reduction of any residual or trace amounts of the solvent from the coating.

In one embodiment, EVAL is used along with DMAC solvent. DMAC is a relatively non-volatile solvent with a boiling point of 166° C. EVAL may be dried at about 80° C., and if higher temperatures are used, it may degrade. When dry, EVAL is very impermeable, even to gases such as oxygen, but the permeability of EVAL is very dependent on its moisture content. Therefore, drying stents in the presence of high humidity effectively removes the residual solvent while retaining the integrity of drugs, such as everolimus. The following Table 1 demonstrates the difference between the amount of residual solvent using a conventional stent drying process versus a humidity bake process.

TABLE 1

| Test # | A | B |
|---|---|---|
| Description | EVAL | EVAL |
| Size | 8 × 100 mm | 8 × 100 mm |
| Process | Existing Process (dry) (pre-sterile) | Existing Process w/ 24 hr Humidity Bake (pre-sterile) |
| Oven Time/ Temp/RH: | 80° C./30 min/ambient (2 cycles) | 80° C./30 min (2 cycles) + 50° C./24 hrs/90% + RH |
| | Residual Solvent (μg) | Residual Solvent (μg) |
| | 322.9 | 2.0 |
| | 353.2 | 1.0 |
| | 314.1 | 0.8 |
| | 317.3 | 0.7 |
| | 318.0 | 1.4 |
| | 336.0 | |
| | 327.2 | |
| | 367.1 | |
| | 321.2 | |
| | 332.3 | |
| Average: | 330.9 | 1.2 |
| StDev: | 17.13 | 0.53 |
| Cumulative Release Rate (% of Target Total Content, Mean) (6/24/168 hrs) | 6 hrs - 30% 24 hrs - 50% 168 hrs - 75% | 6 hrs - 19% 24 hrs - 36% 168 hrs - not tested |

Figure 8:
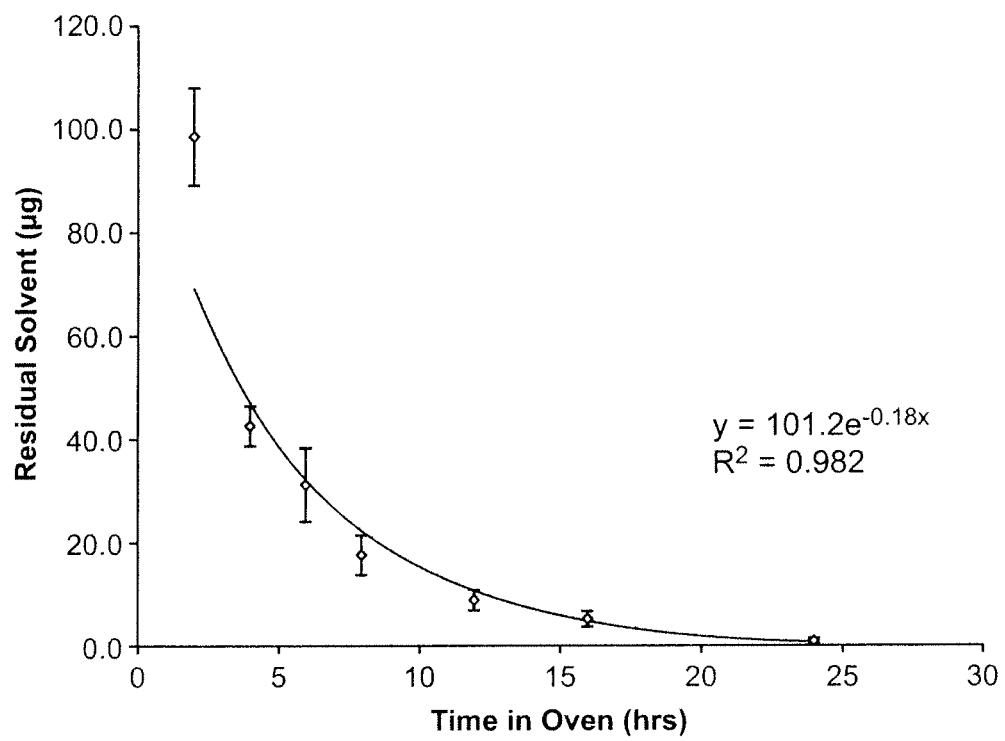
FIG. 8 is a graph illustrating the residual solvent in a coating verses the baking time in an oven.

Table 2 and FIG. 8 demonstrate how the residual solvent content decreases with increased baking time at 50° C. and 80% relative humidity.

TABLE 2

| | Bake Time | | | | | | |
|---|---|---|---|---|---|---|---|
| | 2 | 4 | 6 | 8 | 12 | 16 | 24 |
| RS | 92.5 | 45.9 | 31 | 13.9 | 10.5 | 7.2 | 1.6 |
| | 99.2 | 41.6 | 32.5 | 16.9 | 7.7 | 4.9 | 0.8 |
| | 95.9 | 47.4 | 20.9 | 24.8 | 6.9 | 4.7 | 1.4 |
| | 90.2 | 38.7 | 40.7 | 16.4 | 8.2 | 6.6 | 1.7 |
| | 114.3 | 39.3 | 30.4 | 16.7 | 11.5 | 3.4 | 0.4 |
| Average | 98.4 | 42.6 | 31.1 | 17.7 | 9.0 | 5.4 | 1.2 |
| St. Dev. | 9.51 | 3.91 | 7.05 | 4.13 | 1.95 | 1.53 | 0.56 |
| % RSD | 9.7% | 9.2% | 22.7% | 23.3% | 21.8% | 28.6% | 47.3% |

Bake Time in Hrs.
RS = Residual Solvent (μg)

The maximum amount of remaining residual solvent depends on the size, and in particular, the length of the stent because the diameters are similar. In one embodiment, the maximum residual solvent level for a 30 mm long stent is 45.0 μg; 40 mm long stent is 70.0 μg, 60 mm long stent is 116.0 μg; 80 mm long stent is 177.0 μg; and a 100 mm long stent is 228.0 μg. In another embodiment, the maximum residual in μg=[(stent length (mm))×(2.634)]−(36.08).

In addition to EVAL, the formulation for making the drug-polymer layer can additionally include an active agent or a drug which can be incorporated into the EVAL solution. The amount of the drug can be between about 0.1 and about 10 mass % of the total mass of the formulation used to make the drug-polymer layer. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

The method of the present invention can be used for fabricating stent coatings including polymers that absorb at least about 1 mass % of water when exposed to relative humidity of about 100%. EVAL, which absorbs up to 5 mass % of water when exposed to relative humidity of about 100%, is just one example of a polymer that can be used. Examples of suitable polymers other than EVAL include poly(N-vinylpyrrolidone) (PVP), ethyl cellulose, cellulose acetate, carboxymethyl cellulose, cellulosics, chitin, chitosan, poly(vinyl alcohol), heparin, dextran, dextrin, dextran sulfate, collagen, gelatin, hyaluronic acid, chondroitan sulfate, glycosaminoglycans, poly[(2-hydroxyethyl)methylmethacrylate], polyurethanes, poly(ether urethanes), poly(ester urethanes), poly(carbonate urethanes), thermoplastic polyesters, solvent soluble nylons, poly(acrylamide), poly(acrylic acid), copolymers of acrylic acid and acrylates, poly(methacrylic acid), copolymers of methacrylic acid and methacrylates, and blends thereof. Table 3 is a summary demonstrating which solvents can be used in conjunction with particular polymers in order to fabricate coatings according to embodiments of the present invention.

TABLE 3

Examples of Polymer-Solvent Compositions

| Example | Polymer | Solvents |
|---|---|---|
| 1 | EVAL | DMSO, DMAC, DMF, NMP, formamide, cyclohexanol, sulfolane, benzyl alcohol, phenol, formic acid, m-cresol, p-cresol, trifluoroacetic acid, glycerol, ethylene glycol, propylene glycol |
| 2 | Sodium Heparin | DMSO, DMAC, DMF, NMP, formamide, benzyl alcohol |
| 3 | PVP | Propylene glycol, ethylene glycol, formamide, glycerol, DMSO |
| 4 | Hyaluronic Acid | DMF, DMSO, formamide |
| 5 | Poly(vinyl alcohol) | DMSO, formamide |
| 6 | TECOFLEX 80A poly(ester urethane) | DMAC, DMF |

Pre-Screen Process

According to several embodiments of the invention, to ensure that a given lot of drug eluting stents (DES) produces results within specifications, one or more of the following controls may be used including 1) testing raw materials before using them to insure that the materials meet particular specifications; 2) applying tight tolerances on process parameters, such as temperature and pressure control; and 3) testing the intermediate products throughout the manufacturing process to insure that they are meeting specifications.

One of the critical quality attributes related to DES performance is in vitro release rate. The in vitro release rate correlates to in vivo release rate. The release of the drug at therapeutic levels over a designed time period provides the means to prevent restenosis.

According to one embodiment of the invention, a process is used to provide an accurate means of controlling the release rate for an individual manufactured DES lot. The manufacturing process comprises applying an optional polymer primer coat, a drug/polymer coat, and a polymer final coat to a bare metal stent. The release rate is primarily dependent on the polymer top coat thickness. When the thickness is obtained by spraying several coats at a certain μg weight gain per coat, then the release rate is a function of the number of coats.

According to an embodiment, the pre-screen process involves determining the correct number of top coats that will yield the specified release rate at product lot release. The coating thickness correlates to the number of thin coats applied to make up the total thickness. The pre-screen processes a group of stents through the normal manufacturing process and uses the same drug, polymer and solvent as the manufacturing lot to be built. In some embodiments, different groups of the pre-screen samples are coated with different numbers of final coats and each pre-screen group of stents is then tested for drug release rate. The group with the desired release rate determines how many coats need to be applied. Analysis of the data is fed back to the manufacturing line indicating how many final coats to apply. The main production run then continues to completion.

Figure 9:
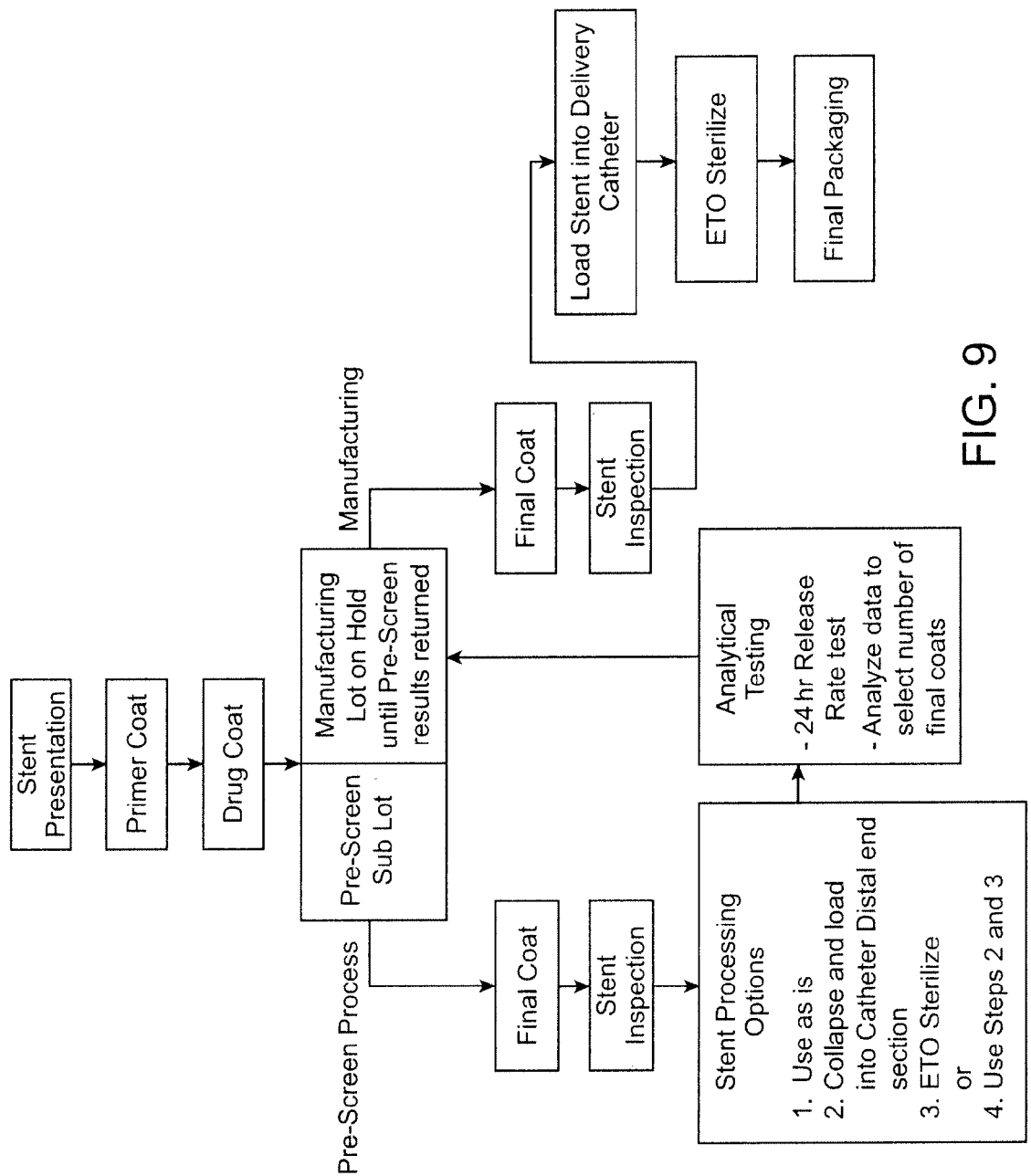
FIG. 9 is a process flow chart illustrating a manufacturing process from stent preparation through final packaging according to an embodiment of the present invention.

According to one embodiment, the manufacturing process from stent preparation through final packaging is illustrated in FIG. 9 and as follows:

Step 1:—All stents for the manufacturing build are inspected and prepared for spraying.

Step 2:—Primer coating is started, first for the pre-screen stents and then continued for the manufacturing build.

Step 3:—Drug coating is started, first for the pre-screen stents and then continued for the manufacturing build.

Step 4:—At this point only the pre-screen stents are processed further. All other stents for the manufacturing build are put on hold until pre-screen results are returned.

Step 5:—Pre-screen stents are processed through the final coat process. Typically 7 stents (3 min to 30 max.) are coated with, e.g., 10 thin coats. This is repeated for, e.g., 12, 14, 16, and 18 coats.

Step 6:—The pre-screen stents go through a final stent and coating inspection

Step 7:—At this stage there are several alternative methods for pre-screen conditioning. One embodiment will be explained here. Other options, including quick sterilization and no sterilization will be discussed below.

The pre-screen stents are collapsed, loaded onto catheters, and TYVEK packaged per the normal manufacturing process.

The assemblies are sterilized per the normal manufacturing process

Step 8:—Pre-screen stents are tested for release rate. The data is analyzed and the number of coats that produces a release rate closest to the release rate specification mean is fed back to the manufacturing line.

Step 9:—The manufacturing lot is then coated with the pre-screen predicted number of final coats.

The manufacturing lot is completed, sterilized, and lot release tested per normal procedures.

Process Advantages:

Small variations of the quality of raw materials and solvent can be corrected for e.g., in the case of polymer, changes in molecular weight distribution and water content can affect the release rate. This is important when the polymer undergoes any additional processing, such as purification, prior to being used. The drug and solvent combination is also susceptible to moisture effects. Another advantage is that products are produced with consistent test results for release rates. A further advantage is to minimize failed lots due to out of a specification release rates.

Testing Method for Pre-screen Process

Release rate testing for lot release involves continuous dipping of DES units in a medium and testing samples at different time points. In one approach, the time points include 2, 6, 12, 24, 36, 48, 72, 96 . . . 168 hr and then every 24 hr until 80% of drug is released. For the pre-screen process, an abbreviated method may be used where sample are tested only at a single time point of 24 hr. This allows faster turn around time yet provides a method of estimating the release profile.

Variations to the Pre-Screen Process

The pre-screen process provides accurate final coat feedback for the manufacturing lot, however it puts the manufacturing build on hold until the pre-screen stents are processed, tested, and the analyzed results are fed back to the manufacturing line. This is of particular concern as coating solutions have shelf lives. Therefore the coating needs to be completed before the solutions' shelf lives expire. The following are various alternatives that are used to shorten the pre-screen cycle time:

Quick Sterilization

ETO sterilization typically has a 7 to 14 day turn around time. A shorter sterilization cycle that eliminates the preconditioning and/or aeration times can reduce the cycle time to 1 day. To use this pre-screen method several trials are needed to correlate the release rate difference between the two cycles. The offset difference can then be applied to the pre-screen results to predict the manufactured lot release rate. For example, several groups of stents with the same coating formulation within each group, with each group having a different coating formulation, are tested for release rate at 1 day, and 7 days or 14 days depending on how the manufacturing lot will be treated. Assuming that the 14 day sterilization is desired, then the 1 day results are compared with the 14 day results. The coating composition on the group of stents that ultimately had the desired release rate after 14 days of sterilization indicate the desired group of day 1 stents, and hence the desired coating composition after 1 day of sterilization.

No Sterilization

In the same way as for quick sterilization, pre-screened stents can be analytically tested as soon as they are final coated and collapsed, or immediately after being final coated. In these cases new offset values are obtained by separate testing. These methods eliminate the 1 to 14 day delays due to sterilization.

Some embodiments of the present invention are illustrated by the following Examples.

Example 1

A polymer solution containing about 4.0 mass % EVAL and the balance, a solvent blend of DMAC and pentane, with a mass ratio between DMAC and pentane of about 4:1 can be prepared. To prepare the polymer solution, EVAL can be combined with DMAC and the mixture can be stirred for about 2 hrs at a temperature of about 80° C. The solution can be applied onto a 13-mm TETRA stent (previously available from Guidant Corp., now Abbott Vascular) to form a primer layer. An additional stent to which the coating may be applied is the ABSOLUTE™: Self-Expandable Peripheral Nitinol Stent (available from Abbott Vascular). To apply the primer layer, a spray apparatus, such as an EFD 780S spray nozzle with a VALVEMATE 7040 control system, manufactured by EFD, Inc. of East Providence, R.I. can be used. The EFD 780S spray nozzle is an air-assisted external mixing atomizer. The composition can be atomized by air and applied to the stent surfaces. The atomization pressure can be about 0.1 MPa (15 psi). During the process of applying the composition, the stent can be rotated about its longitudinal axis, at a speed of about 120 rpm. The stent can be also linearly moved along the same axis during the application.

The EVAL solution can be applied to the 13-mm TETRA in a series of 10-second passes, to deposit about 10 μg of coating per spray pass. Instead of the 13-mm TETRA stent, other suitable stents can also be used, for example, a 12-mm VISION stent (available from Abbott Vascular). Between the spray passes, the stent can be dried for about 10 seconds using flowing air with a temperature of about 60° C. Five spray passes can be applied, followed by baking the primer layer in an oven. As the primer layer contains no active agent, the primer layer can be baked at a temperature at about 140° C. for about 1 hour. Optionally, the relative humidity in the oven during baking can be about 60%. As a result, a primer layer can be formed having a solids content of about 50 μg. "Solids" means the amount of the dry residue deposited on the stent after all volatile organic compounds (e.g., the solvent) have been removed.

A drug-containing formulation can be prepared comprising about 4.0 mass % EVAL, about 1.33 mass % everolimus, and the balance, a solvent blend, the blend comprising DMAC and pentane in a mass ratio of about 4:1. EVAL can be combined with DMAC and the mixture can be stirred for about 2 hrs at a temperature of about 80° C. Pentane and everolimus can then be added to the EVAL solution.

The drug-containing formulation can be sprayed to the primed stent. In a manner identical to the application of the primer layer, 26 spray passes can be performed, depositing about 20 μg of the wet drug-polymer layer per each pass. The wet drug-polymer layer can then be baked in an oven at about 50° C. for about 1 hour, while relative humidity in the oven is maintained at about 60%, to form the dry drug-polymer layer having a solids content of about 460 μg.

Example 2

A primer solution can be prepared and coated onto a 13 mm TETRA stent as described in Example 1. An additional stent to which the coating may be applied is the ABSOLUTE™: Self-Expandable Peripheral Nitinol Stent (available from Abbott Vascular). A drug-containing formulation can be prepared comprising about 4.0 mass % EVAL, about 2.0 mass % paclitaxel, and the balance, a solvent blend of DMAC and tetrahydrofuran (THF), the blend having a mass ratio between DMAC and THF of about 3:2. EVAL can be combined with DMAC and the mixture stirred for about 2 hours at a temperature of about 80° C. THF and paclitaxel can then be added to the EVAL solution.

The drug containing formulation can be sprayed onto the primed stent. In a manner identical to the application of the primer layer, nine spray passes can be performed, depositing about 20 μg of the wet formulation per each spray pass. The wet drug-polymer layer can then be baked in an oven at about 60° C. for about one hour, while the relative humidity in the oven is maintained at about 60%, to form a the drug-polymer layer having a solids content of about 150 μg.

A topcoat formulation can be prepared comprising about 2.2 mass % EVAL, about 1.5 mass % sodium heparin, and the balance, a solvent blend of formamide, methanol and DMAC, the blend having a mass ratio between formamide, methanol and DMAC of about 1:1:3. EVAL can be combined with DMAC and the mixture can be stirred for about 2 hours at a temperature of about 80° C. Sodium heparin can be dissolved in the blend of formamide and methanol. The EVAL solution can then be added to the heparin solution. This topcoat formulation can be sprayed onto the dry drug-polymer layer. In a manner identical to the application of the primer and drug-polymer layers, four spray passes can be performed, depositing about 20 μg of the wet topcoat per spray pass. The wet topcoat layer can then be baked in an oven at about 60° C. for about one hour, while the relative humidity in the oven is maintained at about 60%, to form a topcoat layer having a solids content of about 60 μg.

Example 3

A polymer solution containing about 2.0 mass % of poly (butyl methacrylate) (PBMA) and the balance, a blend of acetone and xylene having a mass ratio between acetone and xylene of about 3:2 can be prepared. To prepare the polymer solution, PBMA can be combined with acetone and the mixture can be stirred for about 1 hour at 60° C., followed by adding xylene. The solution can be sprayed onto a stent to form a primer layer as described in Example 1. The PBMA solution can be applied to a 13-mm TETRA stent in a series of 10-second passes, to deposit about 10 μg of the polymer solution per spray pass. An additional stent to which the coating may be applied is the ABSOLUTE™: Self-Expandable Peripheral Nitinol Stent (available from Abbott Vascular). Between passes, the stent can be dried at ambient temperature for about 10 seconds using flowing air. Five spray passes can be applied, followed by baking the wet primer layer in an oven at about 80° C. for about 30 minutes. As a result, a primer layer can be formed having a solids content of about 50 μg.

A drug-containing formulation can be prepared comprising about 4.0 mass % BIONATE 55D, about 2.0 mass % rapamycin, and the balance, a solvent blend of DMAC and THF, the blend having a mass ratio between DMAC and THF of about 1:1. BIONATE 55D is a trade name of a thermoplastic polycarbonate-urethane elastomer formed as the product of the reaction between a hydroxyl-terminated polycarbonate, an aromatic diisocyanate, and a low molecular weight glycol used as a chain extender. BIONATE 55D is available from The Polymer Technology Group Incorporated of Berkeley, Calif. BIOANATE 55D can be combined with DMAC and the mixture can be stirred for about 6 hrs at a temperature of about 80° C. THF and rapamycin can then be added to the BIONATE 55D solution.

The drug containing formulation can be sprayed onto the primed stent. In a manner identical to the application of the primer layer, 27 spray passes can be performed, depositing about 20 μg per spray pass. The wet drug-polymer layer can then be baked in an oven at about 60° C. for about one hour, while the relative humidity in the oven is maintained at about 60%, to form a the drug-polymer layer having a solids content of about 500 μg.

Example 4

A primer solution can be prepared and coated onto a 13 mm TETRA stent as described in Example 1. An additional stent to which the coating may be applied is the ABSOLUTE™: Self-Expandable Peripheral Nitinol Stent (available from Abbott Vascular). A drug-containing formulation can be prepared and coated on the stent as described in Example 2, except the baking of the wet drug-polymer layer can be carried out at about 100% relative humidity in a sealed vessel. First, a sealed vessel containing deionized water can be placed in an oven set to about 50° C. and allowed to equilibrate. The stent having wet drug-polymer layer coated thereon can be placed into the vessel, followed by closing the vessel and baking at about 50° C. for two hours. The stent is positioned in the vessel in such as way as to not make contact with the deionized water.

Example 5

The following data was obtained by replacing the dry baking with humidity baking

TABLE 4

Release Rate and Residual Solvent vs.
Baking time in humidity chamber (minutes)

| Arm # | Drug Coat Humidity Bake Time (minutes) | Final Coat Humidity Bake time (minutes) | 24 hr. Release Rate Sterile (%) | Residual Solvent (µg) |
|---|---|---|---|---|
| 1 | 30 | 30 | 51.75 | 265 |
| 2 | 60 | 60 | 48 | 188 |
| 3 | 60 | 120 | 60.5 | 152 |
| 4 | 60 | 240 | 58.5 | 83 |

The four Arms of the experiment baked the 8 mm diameter×100 mm long stents for different durations in a humid environment through the drug and final coat processes. Listed in Table 4 are the resultant drug release rate (RR) after 24 hours and residual solvent (RS) content.

The minimum specification for residual solvents for this size stent is 228 µg. Arm 1, which was humidity baked for 30 minutes after the drug coat and 30 minutes after the final coat, had residual solvents slightly higher than the specification. However stents with higher humidity bake times had residual solvents lower than the specification. The release rate in 24 hours was not targeted to a particular value, and the differences are of no concern since the final coat thickness could be adjusted to obtain the required release rate.

The following combinations of oven baking may be employed to reduce the residual solvents to acceptable levels and also simplify and speed up the manufacturing process.

In one embodiment, after at least one drug coat is applied to the stent, the coated stent is dry baked for 30 minutes. Next, at least one final coating formulation is sprayed on top of the drug coat, and after the desired number of coats is sprayed, the stent with the drug coats covered by the final coats is dry baked for 30 minutes. The stent is then collapsed, loaded onto a catheter, and TYVEK packaged. This package is then humidity baked for four hours.

In another embodiment, after at least one drug coat is applied to the stent, the coated stent is humidity baked for 30 minutes. Next, at least one final coating formulation is sprayed on top of the drug coat, and after the desired number of coats is sprayed, the stent with the drug coats covered by the final coats is humidity baked for 30 minutes. The stent is then collapsed, loaded onto a catheter, and TYVEK packaged. This package is then humidity baked for two hours.

In yet another embodiment, after at least one drug coat is applied to the stent, the coated stent is dry baked for 30 minutes. Next, at least one final coating formulation is sprayed on top of the drug coat, and after the desired number of coats is sprayed, the stent with the drug coats covered by the final coats is humidity baked for 30 minutes. The stent is then collapsed, loaded onto a catheter, and TYVEK packaged. This package is then humidity baked for two hours.

In a further embodiment, after at least one drug coat is applied to the stent, the coated stent is dry baked for 30 minutes. Next, at least one final coating formulation is sprayed on top of the drug coat, and after the desired number of coats is sprayed, the stent with the drug coats covered by the final coats is dry baked for four hours. The stent is then collapsed, loaded onto a catheter, and TYVEK packaged. This package is not baked.

In an embodiment, after at least one drug coat is applied to the stent, the coated stent is not baked at this point. Next, at least one final coating formulation is sprayed on top of the drug coat, and after the desired number of coats is sprayed, the stent with the drug coats covered by the final coats is dry baked for four hours. The stent is then collapsed, loaded onto a catheter, and TYVEK packaged. This package is not baked.

Table 5 describes the current parameter settings for each of the baking processes.

TABLE 5

Current Process Conditions

| Process Parameters/ Process name | Temperature (° C.) | Relative Humidity (%) |
|---|---|---|
| Dry Bake for all processes | 80° C. | NA |
| Humidity Bake | 50° C. | 80% |

Example 6

A clinical study to evaluate the safety and performance of the everolimus-eluting self-expanding Nitinol stent system for the treatment of atherosclerotic de novo or restenotic native superficial femoral and proximal popliteal artery lesions was performed. Performance and efficacy was determined and pharmacokinetic evaluation was conducted.

The stent had a drug eluting layer consisting of two layers, a primer layer and a drug/polymer layer. As discussed above, the primer layer is applied to the surface of the stent to aid in the adherence of the drug/polymer matrix to the stent. The drug/polymer matrix layer is composted of EVAL polymer mixed with everolimus. The drug/polymer matrix was applied to the sent on top of the primer layer.

Patients had a single de novo or restenotic native disease segment of the superficial femoral artery (SFA) or proximal popliteal artery (located within the following parameters: 1 cm from the femoral bifurcation of the SFA and 3 cm from the proximal margin of the intercondylar fossa). For inclusion into the trial, the disease segment length was between ≥3 cm (30 mm) and ≤17 cm (170 mm), the target vessel reference diameter was between ≥4.3 mm and ≤7.3 mm with >50% diameter stenosis, all by visual estimation. The inflow artery had to be free from significant lesions (>50% stenosis) by angiography. Patients with a significant iliac artery stenosis were eligible for inclusion into the trial, if the stenosis was successfully treated without complication, prior to patient enrollment and treatment of the target lesion with the investigational device. Patients were required to have a patent popliteal artery free from significant lesion (>50% stenosis) with at least one patent outflow artery that provided in-line circulation to the lower leg and foot, which was confirmed by angiography. For patients with bilateral SFA lesions, the lesion in the highest Rutherford Clinical Category limb was to be treated.

Patients were stented with everolimus-eluting Nitinol stents. The length of the stent used depended on the length of the superficial femoral or proximal popliteal lesions.

Prior to the stenting procedure, patients received one of two medication regimens: 1) aspirin (75 mg daily) and either clopidogrel (75 mg daily) or ticlopidine (250 mg twice a day) for at least 3 consecutive days, or 2) a pre-loading dose of 300-600 mg of clopidogrel or 500 mg of ticlopidine. Post-procedure, patients were required to receive a minimum daily dose of 75 mg of aspirin and either clopidogrel 75 mg (minimum dose) or ticlopidine 250 mg daily (minimum dose) for at least 6 months. Clopidogrel was taken by 97.1% of the patients with a mean duration intake of 171.6±29.3 days, while aspirin was taken by 99.0% of the patients, with a mean duration intake of 170.7±32.4 days. All subjects underwent clinical assessments at 30 days, 6 months and will be followed for 12 months and 18 months after the stenting procedure and annually for five years.

Two sub studies were performed; Pharmacokinetic (PK) and Computed Tomography Angiography (CTA).

Pharmacokinetic evaluation was conducted in a subset of 26 patients who received everolimus-eluting stents. For the 26 patients, there were 18 males and 8 females. The mean age was 66 years (ranging from 50 to 82 years). The target lesion was a single de novo superficial femoral artery (SFA) or proximal popliteal artery with ≥50% stenosis, ≥30 mm and <170 mm lesion length and ≥4.3 mm and ≤7.3 mm target vessel diameter (via visual estimate). All patients received everolimus-eluting stents implanted during the percutaneous femoral intervention procedure.

Blood samples for the evaluation of everolimus concentrations were collected by venpuncture prior to stent implantation and at approximately 1, 4 and 8 hours post final stent placement and before subject discharge from the study site (collection times ranged from 16.92 to 166.45 hours) and at one month after the percutaneous femoral intervention procedure.

Blood concentrations of everolimus were determined using a validated liquid/liquid extraction high performance liquid chromatography (HPLQ method with tandem mass spectrometric detection (MS/MS). The lower limit of quantitation (LLOQ) for everolimus was 0.2 ng/mL using a 0.020 mL (20 µL) blood sample.

The pharmacokinetic parameter values of everolimus were estimated using noncompartmental methods. These included: the maximum observed plasma concentration (Cmax) and time to Cmax (Tmax), the area under the plasma concentration-time curve (AUC) from time 0 to eight hours ($AUC_{0-8}$), 24 hours ($AUC_{0-24}$), 672 hours ($AUC_{0-672}$), time of the last measurable concentration ($AUC_{0-last}$) and dose normalized Cmax, and AUC.

All available plasma concentrations of everolimus and pharmacokinetic parameter values were tabulated for each patient and each dose group, and summary statistics were computed for each sampling time and each parameter. The mean Cmax of everolimus for these dose groups (3033, 3777, 6810 and 7554 µg) ranged from 1.83 to 4.66 ng/mL. The mean $AUC_{0-24}$, and $AUC_{0-last}$, of everolimus for these groups ranged from 36.31 to 72.24 ng-h/mL and from 308.42 to 1571.96 ng-h/mL, respectively. The dose-normalized mean Cmax of everolimus for these dose groups ranged from 0.60 to 0.65 ng/mL/mg. The dose-normalized mean $AUC_{0-24}$, and $AUC_{0-last}$, of everolimus for these dose groups ranged from 7.20 to 12.74 ng-h/mL/mg and from 101.69 to 258.38 to 2 ng-h/mL/mg, respectively.

The present invention may be embodied in other specific forms without departing from its spirit or essential characteristics. The described embodiments are to be considered in all respects only as illustrative and not restrictive. Thus, it is intended that the present invention include modifications and variations that are within the scope of the appended claims and their equivalents. All references recited herein are incorporated herein in their entirety by specific reference.

What is claimed is:

1. A method of coating a plurality of stents comprising:
   a. providing a plurality of pre-screen stents and a plurality of manufacturing build stents, wherein the plurality of pre-screen stents comprises at least two groups of stents and each group has at least two members;
   b. applying a drug coating to the pre-screen stents and the manufacturing build stents;
   c. applying further top coats to only the pre-screen stents, wherein each group of pre-screen stents receives a different number of topcoats than another group receives;
   d. loading the coated pre-screen stents on catheters to form pre-screen stent and catheter assemblies;
   e. sterilizing the loaded pre-screen stent and catheter assemblies;
   f. testing each group of sterilized stents to determine a final number of topcoats necessary to achieve a particular desired release rate;
   g. applying the final number of top coats to the previously drug coated manufacturing build stents to form completed manufacturing build stents;
   h. loading the coated manufacturing build stents on catheters to form manufacturing build stent and catheter assemblies; and
   i. sterilizing the completed manufacturing build stents.

2. The method of claim 1, wherein the release rate testing comprises the continuous dipping the coated pre-screen stents in a medium and measuring the release rates at different time intervals.

3. The method of claim 2, wherein the testing occurs until 80% of the drug is released.

4. The method of claim 2, wherein only a single release rate at 24 hours after the initial dipping is measured.

5. The method of claim 1, wherein the method does not include a primer coat applying step.

6. A method of coating a plurality of stents comprising:
   a. providing a plurality of pre-screen stents and a plurality of manufacturing build stents, wherein the plurality of pre-screen stents comprises at least two groups of stents and each group has at least two members;
   b. applying a drug coating to the pre-screen stents and the manufacturing build stents;
   c. applying further top coats to only the pre-screen stents, wherein each group of pre-screen stents receives a different number of topcoats than another group receives;
   d. testing each group of pre-screen stents to determine a final number of topcoats necessary to achieve a particular desired release rate;
   e. applying the final number of top coats to the previously drug coated manufacturing build stents to form completed manufacturing build stents; and
   f. loading the coated manufacturing build stents on catheters to form manufacturing build stent and catheter assemblies.

7. The method of claim 6, wherein the release rate testing comprises the continuous dipping the coated pre-screen stents in a medium and measuring the release rates at different time intervals.

8. The method of claim 7, wherein the testing occurs until 80% of the drug is released.

9. The method of claim 7, wherein only a single release rate at 24 hours after the initial dipping is measured.

10. The method of claim 6, wherein the method does not include a primer coat applying step.

* * * * *